(12) United States Patent
Adachi et al.

(10) Patent No.: US 8,126,541 B2
(45) Date of Patent: Feb. 28, 2012

(54) DEVICE AND METHOD FOR DECIDING NECESSITY OF BRAINWAVE IDENTIFICATION

(75) Inventors: Shinobu Adachi, Osaka (JP); Koji Morikawa, Kyoto (JP)

(73) Assignee: Panasonic Corporation, Osaka (JP)

( * ) Notice: Subject to any disclaimer, the term of this patent is extended or adjusted under 35 U.S.C. 154(b) by 613 days.

(21) Appl. No.: 12/302,642

(22) PCT Filed: Mar. 13, 2008

(86) PCT No.: PCT/JP2008/000582
§ 371 (c)(1),
(2), (4) Date: Nov. 26, 2008

(87) PCT Pub. No.: WO2008/117521
PCT Pub. Date: Oct. 2, 2008

(65) Prior Publication Data
US 2009/0270753 A1    Oct. 29, 2009

(30) Foreign Application Priority Data
Mar. 28, 2007 (JP) ................................ 2007-085004

(51) Int. Cl.
*A61B 5/0476* (2006.01)
*A61B 5/05* (2006.01)
*G06F 3/01* (2006.01)
*G06F 3/048* (2006.01)

(52) U.S. Cl. ...................................... 600/544

(58) Field of Classification Search .................. None
See application file for complete search history.

(56) References Cited

U.S. PATENT DOCUMENTS
2004/0097824 A1   5/2004   Kageyama
2005/0008733 A1   1/2005   Bae et al.
2006/0101079 A1   5/2006   Morikawa et al.

FOREIGN PATENT DOCUMENTS
JP   10-146323    6/1998
JP   2003-248541  9/2003
JP   2004-152002  5/2004
JP   2004-178363  6/2004
WO   2005/001677  1/2005

OTHER PUBLICATIONS

Notice of Reasons for Rejection for corresponding Japanese Application No. 2009-506203 issued Jun. 22, 2010 and English translation.
Makoto Arizawa, "How computer sciences should be studied 15,"Leading fields of computer sciences (2), bit, Kyoritsu Shuppan Co., Ltd., Jul. 1, 1992, vol. 24, No. 7, pp. 780-787 and partial English translation.
International Search Report for corresponding Application No. PCT/JP2008/000582 mailed May 1, 2008.
Form PCT/ISA/237 and partial English Translation, May 2, 2008.
Emanuel Donchin et al., "The Mental Prosthesis: Assessing the Speed of a P300-Based Brain-Computer Interface", IEEE Transactions on Rehabilitation Engineering, vol. 8, No. 2, Jun. 2000, pp. 174-179.
Xiaorong Gao et al., "A BCI-Based Environmental Controller for the Motion-Disabled", IEEE Transactions on Neural Systems and Rehabilitation Engineering, vol. 11, No. 2, Jun. 2003, pp. 137-140.

*Primary Examiner* — Michael Borin
(74) *Attorney, Agent, or Firm* — Renner, Otto, Boisselle & Sklar, LLP

(57) ABSTRACT

In a system having an interface which utilizes electroencephalogram, it is determined whether the user was looking at a menu or not based on the frequency of the user electroencephalogram, and the electroencephalogram is excluded from the subject of distinction in the case where the user is not looking at the menu.

A distinction necessity determination apparatus 10 for determining whether or not to perform a distinction of an electroencephalogram signal in an electroencephalogram interface system 1 includes a frequency analysis section 11 for calculating a representative frequency at which frequency power of the electroencephalogram signal becomes maximal, and a determination section 12. Based on a relative quantity between the switching frequency of menu items and the representative frequency of the electroencephalogram signal, the determination section 12 determines whether the representative frequency is related to switching of the menu items or not, and based on the result of determination, outputs to an electroencephalogram interface section 100 an instruction to adjust the distinction method for the electroencephalogram signal to be adopted in the electroencephalogram interface section 100.

19 Claims, 12 Drawing Sheets

*FIG.5*
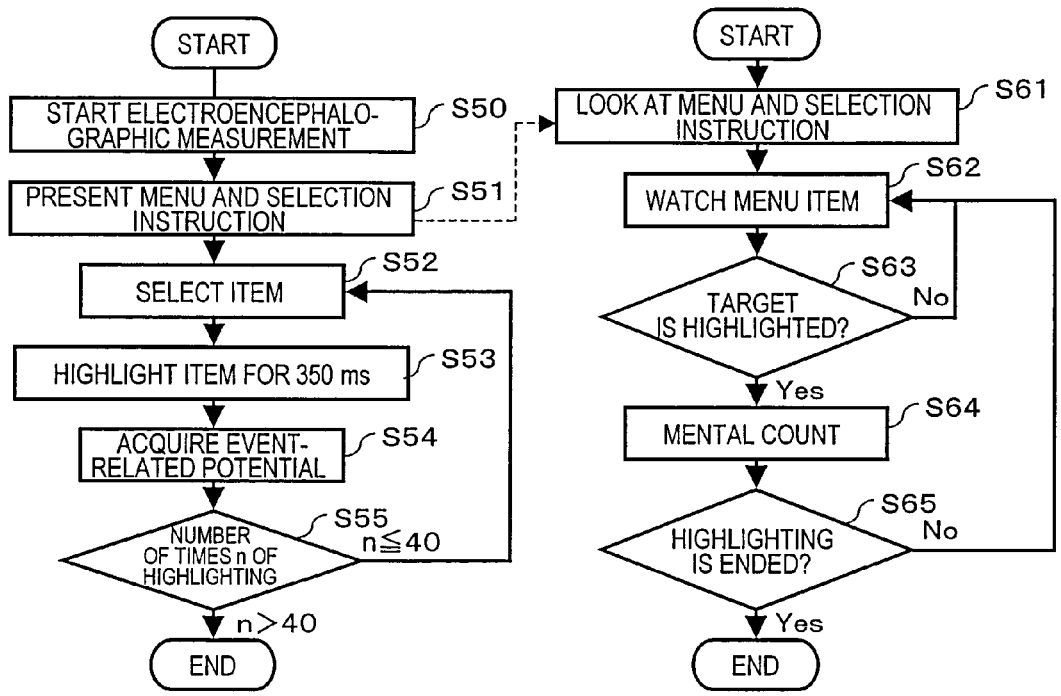
(a) FLOW ON DEVICE SIDE
(b) FLOW ON TEST SUBJECT SIDE
*FIG.6*
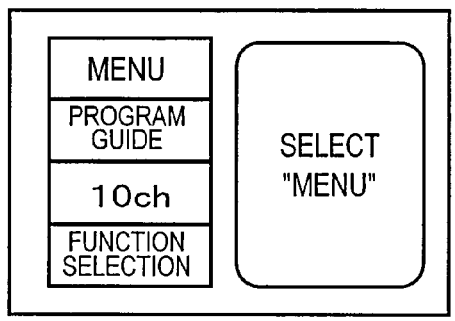
(a) MENU AND SELECTION INSTRUCTION ARE PRESENTED
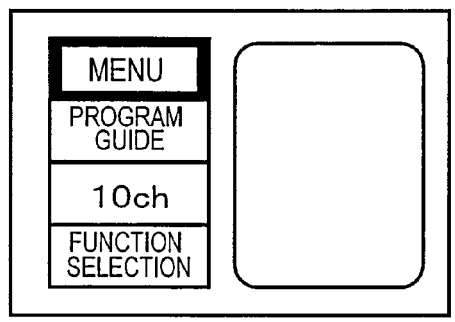
(b) EXAMPLE OF MENU ITEM HIGHLIGHT a: WAVEFORM OF SAMPLE WHERE TARGET IS HIGHLIGHTED AT 0ms
b: WAVEFORM OF SAMPLE WHERE ITEM OTHER THAN TARGET IS HIGHLIGHTED (a) MENU ITEMS ARE SWITCHED
(b) MENU ITEMS ARE NOT SWITCHED

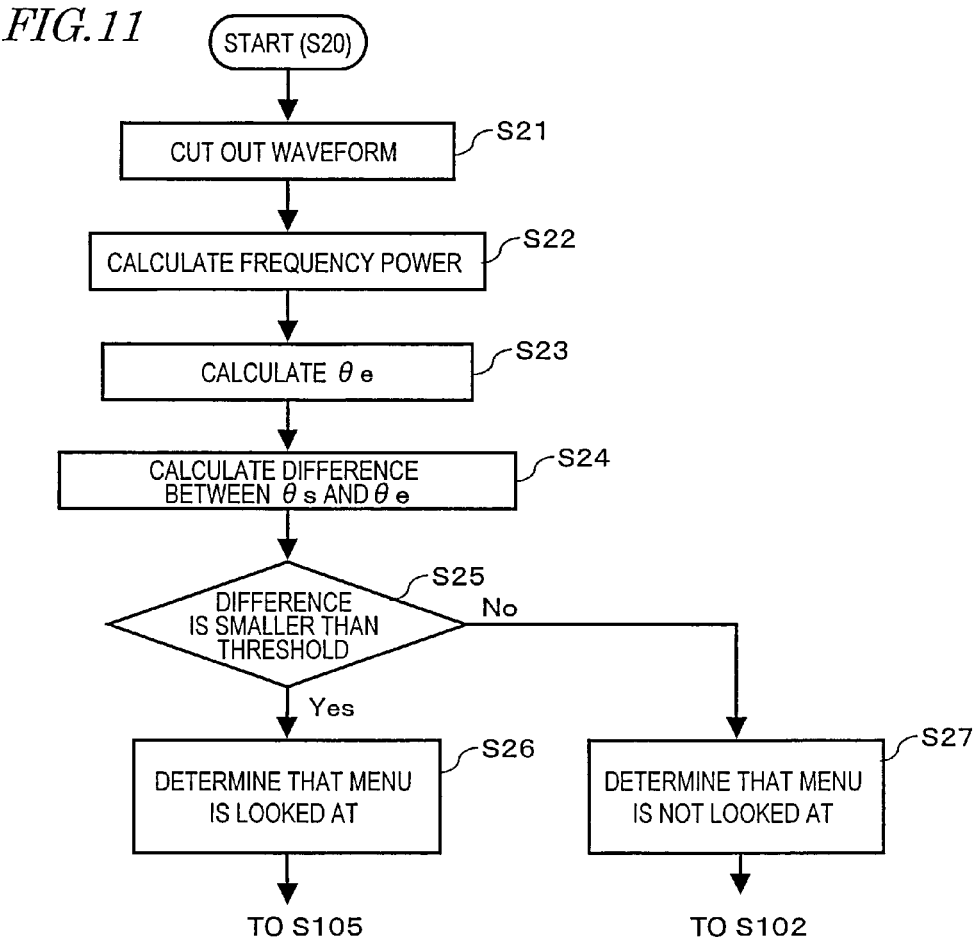
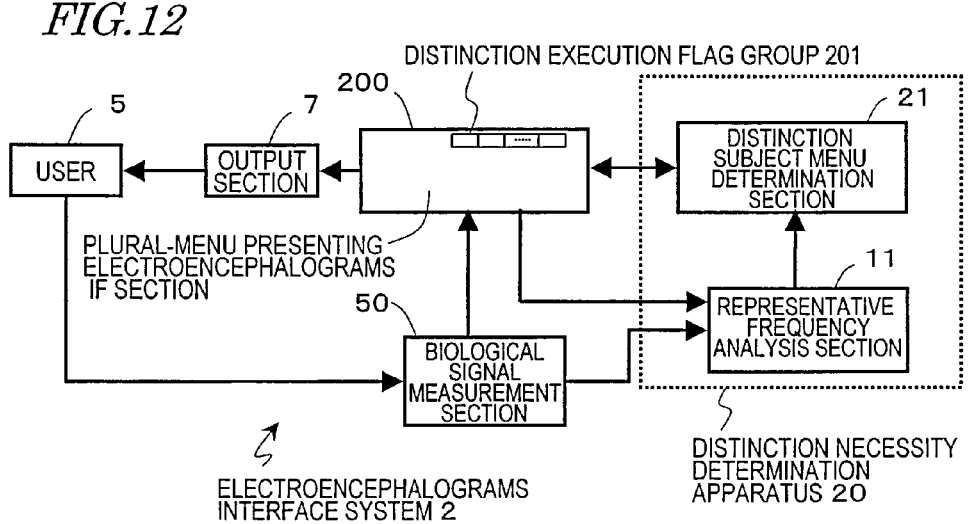

DEVICE AND METHOD FOR DECIDING NECESSITY OF BRAINWAVE IDENTIFICATION

TECHNICAL FIELD

The present invention relates to an interface (an electroencephalogram interface) system which allows a user to manipulate a device by utilizing the electroencephalogram of the user. More specifically, the present invention relates to a technique for, in order to precisely analyze a user's intent, measuring in real time the electroencephalogram of the user when using the electroencephalogram interface, and using that frequency to determine whether the user is looking at a menu item or not.

BACKGROUND ART

In recent years, various types of information devices such as television sets, mobile phones, PDAs (Personal Digital Assistants) have gained prevalence and entered into people's lives. Thus, users need to manipulate information devices in many scenes of their usual lives. Usually, in realizing a device manipulation, a user utilizes a hand to input an input command via an input means (interface section) such as a button. However, in situations where both hands are full because of tasks other than a device manipulation, e.g. household chores, rearing of children, or driving, it is difficult to make an input by using an interface section and it is impossible to realize a device manipulation. Therefore, there are increasing needs of users to manipulate information devices in every kind of situation.

In answer to such needs, input means utilizing biological signals from a user has been developed. For example, Non-Patent Document 1 discloses an electroencephalogram interface that utilizes an event-related potential of electroencephalogram for distinguishing an option which a user wishes to select. To specifically describe the technique described in Non-Patent Document 1, options are randomly highlighted, and a P3 component of an event-related potential which appears about 300 ms after a point in time that an option was highlighted is utilized to enable distinction of the option which the user wishes to select. According to this technique, a user is able to identify an option which he or she wishes to select, without using a hand.

As used herein, an "event-related potential" refers to a transient potential fluctuation in the brain which occurs in temporal relationship with an external or internal event. An electroencephalogram interface utilizes an event-related potential which is obtained from a stimulation to the visual sense as an external event. For example, within the event-related potential for a visual stimulation, a so-called P3 component may be utilized to perform processing such as switching of channels, selection of a program genre of which viewing is desired, and sound volume level adjustment. The "P3 component" refers to a positive component of the event-related potential which appears in a time slot of 250 ms to 500 ms after a target stimulation is presented, regardless of the type of sensory stimulation such as auditory sense, visual sense, or somatic sensation.

For an application of the event-related potential to an interface, it is important to distinguish the event-related potential (e.g., the P3 component) of a subject with a high accuracy. Therefore, it is necessary to accurately measure a biological signal and accurately distinguish the measured biological signal with an appropriate distinction technique.

There are two factors that may lower the distinction ratio. A first factor is that an electroencephalogram component (e.g., the P3 component) which is used for an electroencephalogram interface has a low signal-to-noise ratio (S/N ratio) and a low distinction technique accuracy, so that a highly accurate distinction has not been realized. Regarding this factor, a method for removing the noise mixed in the electroencephalogram and a highly accurate distinction method are both being under development.

For example, Patent Document 1 discloses a technique of improving the distinction ratio which uses a band-pass filter to remove, among the noises contained in the electroencephalogram, noises that are mixed at a frequency different from the frequency of a subject of distinction (event-related potential), e.g., noises on commercial power, and thereafter performs distinction. Patent Document 2 discloses, as a technique of removing noises from living organisms which are difficult to remove with a simple frequency filter, e.g., electro-oculographic potential, a technique of excluding any samples containing an electro-oculographic potential from the subject of distinction, thus obtaining an improved distinction ratio.

A second factor that may lower the distinction ratio is that, depending on the state of the test subject, for example, no electroencephalogram component that serves as a subject of distinction may appear in the electroencephalogram of the test subject, thus making it impossible to perform distinction. Regarding this factor, conventional experiments under laboratory room conditions have adopted a technique of controlling the state of the test subject by instructing the test subject to concentrate on the task by providing a laboratory room which is free of disturbances, or causing the test subject to press a confirmation button, etc., thus allowing a response to steadily appear.

[Patent Document 1] Pamphlet of International Laid-Open No. 2005/001677

[Patent Document 2] Japanese Laid-Open Patent Publication No. 10-146323

[Non-Patent Document 1] Emanuel Donchin and two others, "The Mental Prosthesis: Assesing the Speed of a P300-Based Brain-Computer Interface", TRANSACTIONS ON REHABILITATION ENGINEERING 2000, Vol. 8, June 2000

DISCLOSURE OF INVENTION

Problems to be Solved by the Invention

When electroencephalogram is utilized by a manipulation interface of an information device that is in common use within a household, the user may not always be concentrating on the task of menu selection. For example, situations may occur where, even though a screen of an electroencephalogram interface is being presented, the user is distracted by something else and is not looking at the menu. In such situations, no electroencephalogram component that serves as a subject of distinction appears, thus making it impossible to perform distinction based on electroencephalogram. This precisely corresponds to the aforementioned second factor that may lower the distinction ratio.

When the user is not looking at a menu item, the P3 component does not appear even if a menu item which the user wishes to select is highlighted. However, if the noise having a waveform which resembles the P3 component is accidentally mixed, an erroneous distinction of the P3 component may be made. Since the distinction ratio of electroencephalogram is lowered, a menu item that is not intended by the user may be selected, and thus the electroencephalogram distinction utilizing the electroencephalogram interface may not accurately function. Such an inappropriate recognition is expected to occur often in a situation where electroencephalogram is measured in daily life and utilized for the interface.

The aforementioned problem is not accounted for in experiments under laboratory room conditions, and was first recognized when an electroencephalogram interface was adopted for an information device in common use within a household. It would hinder casual use of an electroencephalogram interface and thus is impossible to create in all general households an environment where the state of the test subject is controlled to allow electroencephalogram responses to steadily appear, as adopted in the experiments under laboratory room conditions. Therefore, other methods that doe not lower the distinction ratio of electroencephalogram are needed.

An objective of the present invention is, in a system having an interface which utilizes electroencephalogram, determine whether the user was looking at a menu or not based on the frequency of the user electroencephalogram, and excludes the case where the user is not looking at the menu from the subject of distinction, thus reducing device operations that are not intended by the user, which are due to erroneous distinction.

Means for Solving the Problems

An apparatus according to the present invention is, in an electroencephalogram interface system having an output section for visually presenting a manipulation menu for a device, a biological signal measurement section for acquiring an electroencephalogram signal from a user, and an electroencephalogram interface section for presenting via the output section menu items of the manipulation menu with a specific switching frequency, distinguishing based on the electroencephalogram signal preliminarily held a component of an event-related potential which is contained in the electroencephalogram signal after each menu item is highlighted, and operating the device based on the distinguished event-related potential, an apparatus for adjusting a distinction method for the electroencephalogram signal to be adopted in the electroencephalogram interface section, comprising: a frequency analysis section for calculating as a representative frequency at which a frequency power of the electroencephalogram signal becomes maximal; and a determination section for, based on a relative quantity between the switching frequency of the menu items and the representative frequency of the electroencephalogram signal, determining whether the representative frequency is related to switching of the menu items or not, and in accordance with the result of determination, outputting to the electroencephalogram interface section an instruction to adjust the distinction method for the electroencephalogram signal to be adopted in the electroencephalogram interface section.

The determination section may instruct the electroencephalogram interface section to adopt the electroencephalogram signal as subject of distinction when the representative frequency is determined as being related to switching of the menu items, and instruct the electroencephalogram interface section to exclude the electroencephalogram signal from the subject of distinction when the representative frequency is determined as not being related to switching of the menu items.

Based on a difference between the switching frequency of menu items and the representative frequency of the electroencephalogram signal, or a ratio between the switching frequency of menu items and the representative frequency of the electroencephalogram signal, the determination section may determine whether the representative frequency is related to switching of the menu items or not.

The frequency analysis section may calculate the representative frequency based on an electroencephalogram signal acquired at or after a point in time which is a predetermined number of seconds before a point of highlighting each menu item.

As the representative frequency, the frequency analysis section may calculate a frequency at which the frequency power becomes largest in a predetermined frequency band containing the switching frequency of menu items.

As the representative frequency, the frequency analysis section may calculate a frequency at which the frequency power becomes largest in a frequency band of 0.5 Hz or above.

The determination section may determine whether the representative frequency is related to switching of the menu items or not based on a relative quantity of the switching frequency being selected from a frequency band of 0.5 Hz to 9 Hz and the representative frequency of the electroencephalogram signal.

The determination section may determine that the representative frequency is not related to switching of the menu items when a difference between the switching frequency of menu items and the representative frequency of the electroencephalogram signal is 0.2 Hz or more.

When the determination section instructs the electroencephalogram interface section to exclude the electroencephalogram signal from the subject of distinction, the electroencephalogram interface section may set back an operating state of the device by one.

When the electroencephalogram interface section presents menu items of a plurality of kinds of manipulation menus at a plurality of respectively different switching frequencies, the determination section may determine whether or not the representative frequency is related to the switching of any one of the menu items of the manipulation menus based on a relative quantity between each of the plurality of switching frequencies and the representative frequency of the electroencephalogram signal.

The determination section may determine whether or not the representative frequency is related to the switching of any one of the menu items of the manipulation menus based on a relative quantity between each of the plurality of switching frequencies being set so as not to be integer multiples of one another and the representative frequency of the electroencephalogram signal.

The determination section may identify a switching frequency corresponding to a smallest relative quantity among relative quantities between the plurality of switching frequencies and the representative frequency of the electroencephalogram signal, and determine whether or not the representative frequency is related to switching of the menu items presented at the identified switching frequency.

The determination section may retain a threshold value corresponding to each of the plurality of switching frequencies; and the determination section may determine that the representative frequency is related to switching of the menu items presented at the identified switching frequency when the smallest relative quantity is smaller than the threshold value corresponding to the identified switching frequency, and determine that the representative frequency is not related to switching of the menu items presented at the identified switching frequency when the smallest relative quantity is equal to or greater than the threshold value corresponding to the identified switching frequency.

The electroencephalogram interface section may retain a threshold value for distinguishing whether a P3 component is contained in the event-related potential contained in the electroencephalogram signal after each menu item is highlighted; and when it is determined that the representative frequency is not related to switching of the menu items, the determination section may change the size of the threshold value in a direction such that the P3 component of the event-related potential becomes less likely to be detected.

A method according to the present invention is, in an electroencephalogram interface system having an output section for visually presenting a manipulation menu for a device, a biological signal measurement section for acquiring an electroencephalogram signal from a user, and an electroencephalogram interface section for presenting via the output section menu items of the manipulation menu with a specific switching frequency, distinguishing based on the electroencephalogram signal preliminarily held a component of an event-related potential which is contained in the electroencephalogram signal after each menu item is highlighted, and operating the device based on the distinguished event-related potential, a method for determining whether or not to allow the electroencephalogram interface section to perform a distinction of the electroencephalogram signal, comprising the steps of: calculating as a representative frequency at which a frequency power of the electroencephalogram signal becomes maximal; and determining whether the representative frequency is related to switching of the menu items or not, based on a relative quantity between the switching frequency of menu items and the representative frequency of the electroencephalogram signal; instructing, when it is determined as being related, the electroencephalogram interface section to adopt the electroencephalogram signal as subject of distinction; and instructing, when it is determined as not being related, the electroencephalogram interface section to exclude the electroencephalogram signal from the subject of distinction.

When the electroencephalogram interface section presents menu items of a plurality of kinds of manipulation menus at a plurality of respectively different switching frequencies, the determining step may determine whether or not manipulation menu the representative frequency is related to the switching of the menu items of the manipulation menus based on a relative quantity between each of the plurality of switching frequencies and the representative frequency of the electroencephalogram signal.

The determining step may identify a switching frequency corresponding to a smallest relative quantity among relative quantities between the plurality of switching frequencies and the representative frequency of the electroencephalogram signal, and determine whether the representative frequency is related to switching of the menu items presented at the identified switching frequency.

A step of providing a threshold value for each of the plurality of switching frequencies may be further comprised, wherein, the determining step may determine that the representative frequency is related to switching of the menu items presented at the identified switching frequency when the smallest relative quantity is smaller than the threshold value corresponding to the identified switching frequency, and determine that the representative frequency is not related to switching of the menu items presented at the identified switching frequency when the smallest relative quantity is equal to or greater than the threshold value corresponding to the identified switching frequency.

Another apparatus according to the present invention is, in an electroencephalogram interface system having an output section for visually presenting a manipulation menu for a device, a biological signal measurement section for acquiring an electroencephalogram signal from a user, and an electroencephalogram interface section for presenting via the output section menu items of the manipulation menu with a specific switching frequency, distinguishing based on the electroencephalogram signal preliminarily held a component of an event-related potential which is contained in the electroencephalogram signal after each menu item is highlighted, and operating the device based on the distinguished event-related potential, an apparatus for adjusting a distinction method for the electroencephalogram signal to be adopted in the electroencephalogram interface section, comprising: a frequency analysis section for calculating as a representative frequency at which a frequency power of the electroencephalogram signal becomes maximal; and a determination section for, based on a relative quantity between the switching frequency of menu items and the representative frequency of the electroencephalogram signal, determining whether the representative frequency is related to switching of the menu items or not, judging that the user is looking at the menu item when the representative frequency is determined as being related and judging that the user is not looking at the menu item when the representative frequency is determined as not being related, and adjusting the distinction method of the electroencephalogram interface section for the electroencephalogram signal in accordance with the result of determination.

Effects of the Invention

With an apparatus and method for distinction necessity determination and an electroencephalogram interface system incorporating the distinction necessity determination apparatus according to the present invention, the distinction method is adjusted by a method of, when a representative frequency ($\theta e$) at which the frequency power of user electroencephalogram becomes maximal is different from a switching frequency ($\theta s$) of menu item highlights, determining that user is not looking at the menu and excluding the case from the subject of distinction. As a result, erroneous distinctions due to overlooking of menu items, which would be a problem in an interface which measures electroencephalogram in daily life, are eliminated, whereby a high distinction ratio can be maintained. As a result, device operations that are not intended by the user, which are caused by misdistinction of electroencephalogram, are reduced, so that the electroencephalogram interface can realize an improved manipulability.

BRIEF DESCRIPTION OF DRAWINGS

FIG. 5 A diagram showing an experimental procedure, where (a) is a flowchart showing a processing procedure by the device, and (b) is a flowchart showing an procedure of action by a test subject.

FIG. 6 (a) is a diagram showing a display screen of a menu and a selection instruction which were actually presented to a test subject, and (b) is a diagram showing an example of displaying a highlighted menu item.

FIG. 11 A flowchart showing a detailed procedure of a process of determining whether the user 5 has been looking at a menu item or not.

FIG. 12 A diagram showing a functional block construction of an electroencephalogram interface system 2 according to Embodiment 2 of the present invention.

Figure 1:
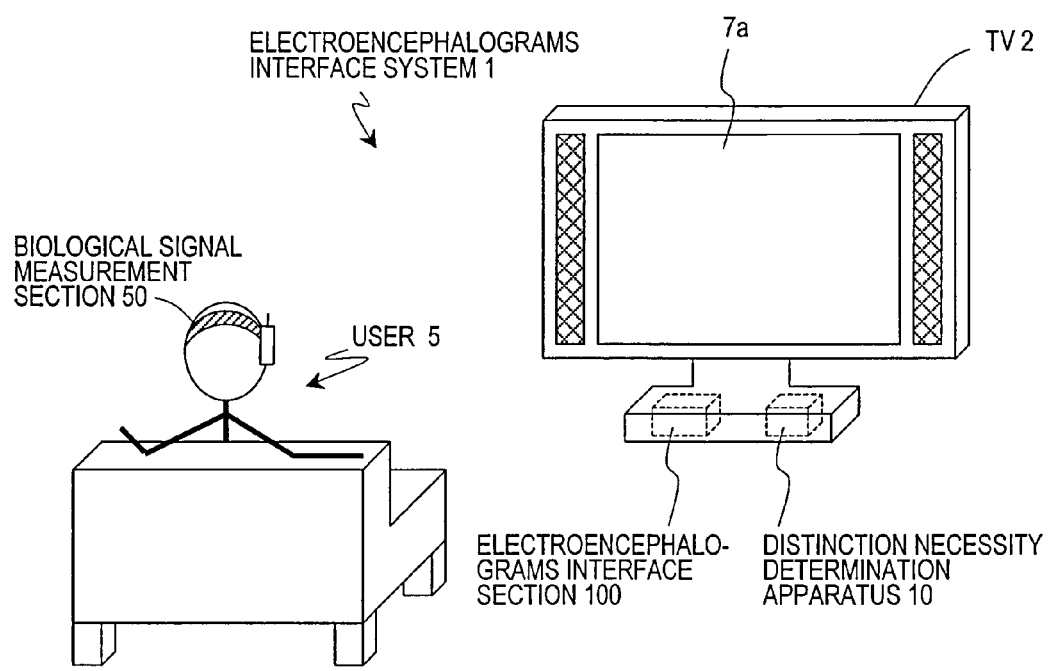
FIG. 1 A diagram showing a construction and an environment of use for an electroencephalogram interface system 1.

DESCRIPTION OF THE REFERENCE NUMERALS 1, 2, 3 electroencephalogram interface system
5 user
7 output section
7a screen
10 distinction necessity determination apparatus
11 representative frequency analysis section
12 determination section
21 distinction subject determination section
31 distinction method adjustment section
50 biological signal measurement section
100 electroencephalogram interface section
200 plural-menu presenting electroencephalogram interface section
300 variable distinction parameter electroencephalogram interface section
301 P3 distinction parameter

BEST MODE FOR CARRYING OUT THE INVENTION

Hereinafter, with reference to the attached drawings, embodiments of an electroencephalogram interface system and a distinction necessity determination apparatus to be incorporated in an electroencephalogram interface system according to the present invention will be described.

Hereinafter, the electroencephalogram interface system will be first described, followed by a description of the construction and operation of the distinction necessity determination apparatus.

FIG. 1 illustrates a construction and an environment of use for the electroencephalogram interface system 1. The electroencephalogram interface system 1 is exemplified so as to correspond to a system construction of Embodiment 1 described later.

The electroencephalogram interface system 1 is a system for providing an interface for manipulating a TV 2 by utilizing an electroencephalogram signal from a user 5. an electroencephalogram signal from the user 5 is acquired by a biological signal measurement section 50 which is worn on the head of the user, and transmitted to an electroencephalogram interface section 100 in a wireless or wired manner. The electroencephalogram interface section 100 internalized in the TV 2 recognizes an intent of the user by utilizing a component called an event-related potential, which constitutes a part of the electroencephalograms, and performs processes such as switching of channels.

Figure 2:
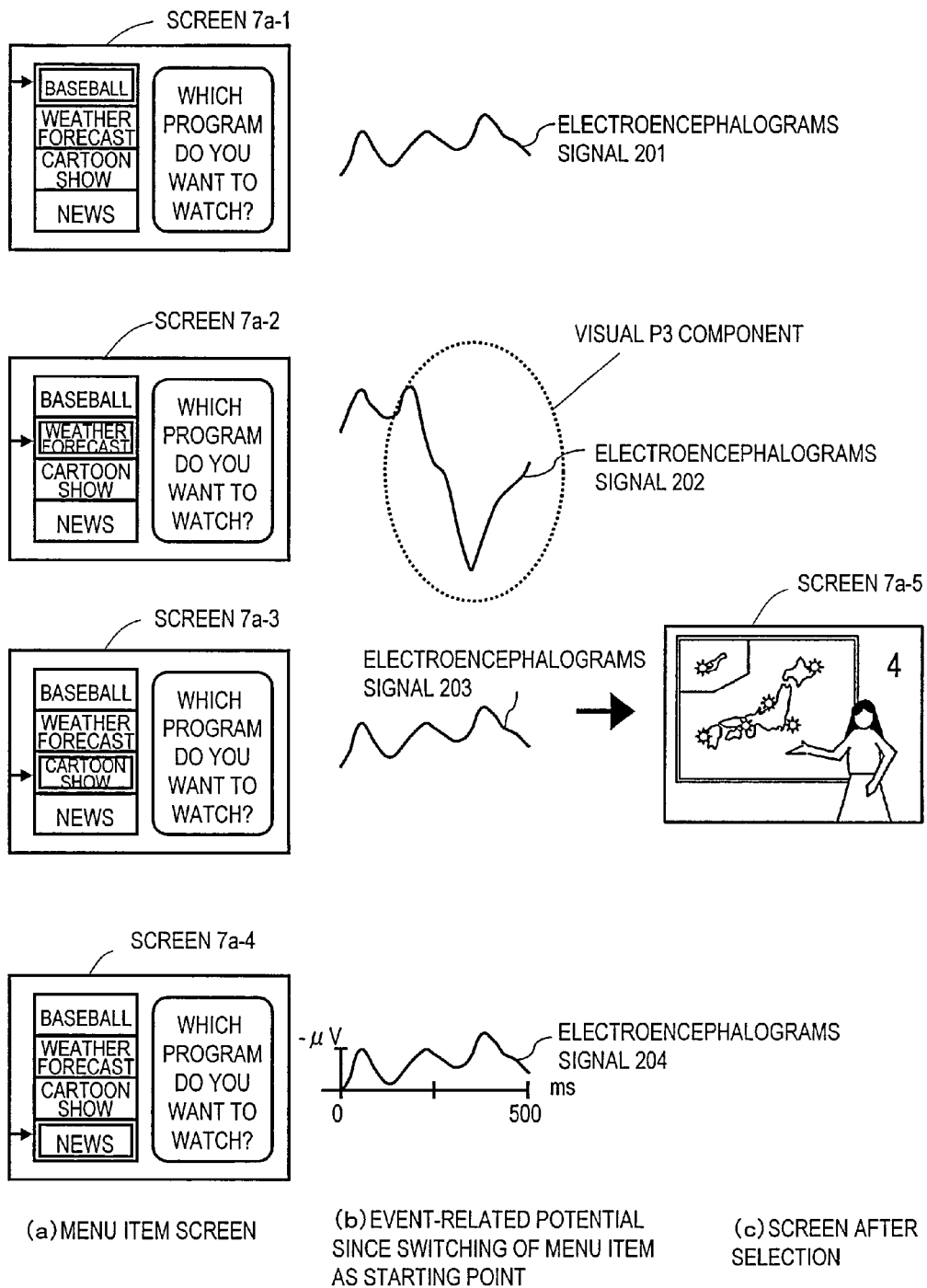
FIG. 2 A diagram showing an example where a TV 2 is manipulated in the electroencephalogram interface system 1 and a user 5 watches a program of a genre which he or she wishes to view.

FIG. 2 shows an example where the TV 2 is manipulated in the electroencephalogram interface system 1 and the user 5 watches a program of a genre which he or she wishes to view.

FIG. 2(a) is an exemplary menu which the electroencephalogram interface section 100 presents to the user via a screen 7a of the TV 2. In FIG. 2(a), a screen 7a-1 to a screen 7a-4 respectively illustrate how menu items "baseball", "weather forecast", "cartoon show", and "news" are highlighted in order or at random.

In the present specification, a group of options concerning device manipulations shown in FIG. 2(a) is collectively defined as a "menu", whereas the respective options constituting the menu are defined as "menu items". Moreover, the frequency with which highlighting of the menu items is switched is defined as a "switching frequency ($\theta$s)". For example, in the case where highlighting is switched twice in one second, the switching frequency ($\theta$s) is 2 Hz (the period being 500 ms). In the following descriptions, it is assumed that the switching frequency ($\theta$s) is 2.86 Hz and that the period is 350 ms.

By highlighting menu items, it becomes possible to measure the event-related potential since a point of highlighting each menu item as a starting point. Note that, instead of highlighting, or in addition to highlighting, a menu item may be presented by a pointer using an auxiliary arrow. FIG. 2(a) illustrates an example where a menu item is presented by highlighting and with a pointer.

FIG. 2(b) schematically shows the event-related potential of an electroencephalogram signal from the user which is measured since a point of highlighting a menu item as a starting point. It is assumed that the user is currently wishing to watch "weather forecast". Among electroencephalogram signals 201 to 204 respectively corresponding to the screen 7a-1 to the screen 7a-4, if the user 5 looks at the screen 7a-2 in which "weather forecast" is highlighted, a characteristic positive component (P3 component) appears with a latency of about 400-450 ms since the point of highlighting "weather forecast" as a starting point (Non-Patent Document 1).

When the electroencephalogram interface section 100 distinguishes this appearance of the P3 component, selection of the menu item "weather forecast" which the user wishes to select becomes possible. FIG. 2(c) shows the screen 7a-5, which comes after the channel has been switched to "weather forecast" as a result of distinguishing the P3 component.

Figure 3:
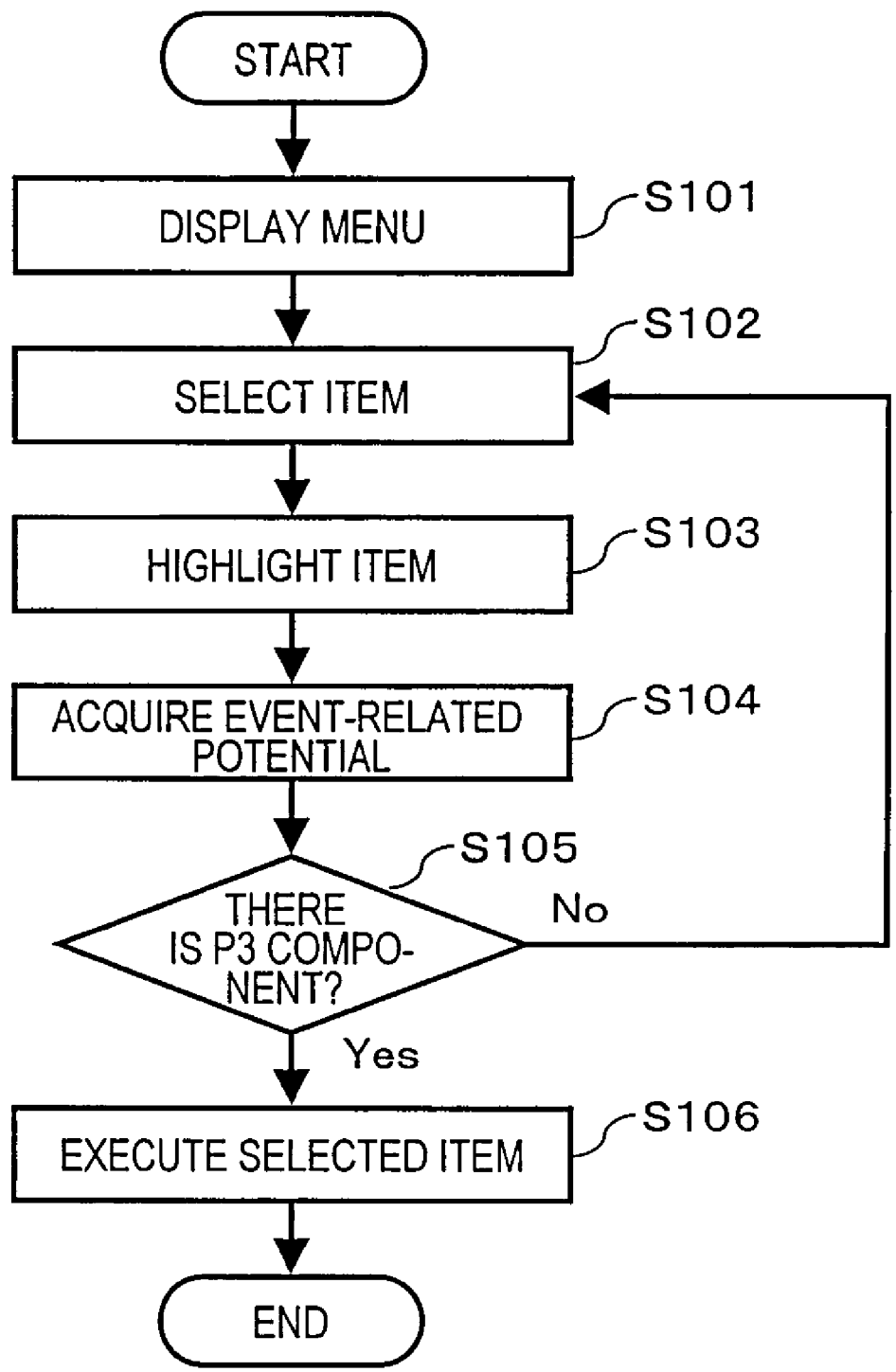
FIG. 3 A flowchart showing an example of a first usual processing procedure by an electroencephalogram interface according to the present invention (processing procedure A).

FIG. 3 shows an example of a first usual processing procedure by the electroencephalogram interface according to the present invention (processing procedure A).

At step S101, the electroencephalogram interface section 100 presents a menu (the left-hand side of FIG. 2(a)) containing e.g. four menu items and an inquiring sentence (the right-hand side of FIG. 2(a)). At step S102, the electroencephalogram interface section 100 selects one of the menu items. At step S103, the menu item selected at step S102 is highlighted.

At step S104, the electroencephalogram interface section 100 measures the event-related potential of the user for the duration of e.g. 500 ms since the point of highlighting a menu item at step S103 as a starting point. The zone to be cut out as the event-related potential may be e.g. 800 ms, 1000 ms, so long as the P3 component appearing at 300-500 ms is contained therein. Herein, event-related potentials 201 to 204 of the electroencephalogram signals schematically shown in FIG. 2(b) are measured.

At step S105, distinction is made as to whether the P3 component is contained in the event-related potential measured at step S104 or not. Distinction of the P3 component may be made by simply determining whether the maximum amplitude of the waveform or an average potential of a given zone of the waveform is greater than a threshold value which is previously set, or as described in Patent Document 2, a correlation coefficient may be calculated with respect to a template which is generated from an arithmetic mean waveform of the P3 component that has been measured with respect to each user in advance. Note that a threshold value may be determined with respect to each user. If Yes at step S105, control proceeds to step S106; if No, control returns to step S102 and the next menu item is selected.

At step S106, the electroencephalogram interface section 100 executes a process corresponding to the menu item selected at step S105. As a result, that menu item is selected and executed, whereby the screen 7a-5 shown in FIG. 2(c) is displayed. For example, in the example of FIG. 2, weather forecast is selected, and the weather forecast program is being presented.

In accordance with the electroencephalogram interface system 1 as such, the user is able to manipulate a device such as the TV 2 without using a hand, even in the case where their both hands are full due to a household chore or rearing of children, for example. Thus, the manipulability of the device is significantly improved.

However, in the case where electroencephalograms are used as an interface, the user may not always be looking at the menu. For example, when any task other than a device manipulation using the electroencephalogram interface (e.g. household chores or rearing of children) is being performed in parallel, it is difficult to always watch the screen of the interface. Moreover, as described earlier, if the user is not looking at the menu at the timing when a menu item is highlighted, the P3 component is not measured at step S103. Under such a situation, if a noise (e.g. electro-oculographic potential) mixes into the event-related potential acquired at step S104 and exhibits a waveform resembling the P3 component, there is a possibility that step S105 may determine that the P3 component exists and that a menu item which is not intended by the user may be selected at step S106. Therefore, it is preferable to perform a process with a higher distinction accuracy.

As a different distinction method, it is possible to use a processing procedure (processing procedure B) which compares the event-related potentials after the respective menu items are highlighted, and selects one that possesses the highest possibility that the P3 component has appeared, for example. When processing procedure B is employed, it is possible to select what is close to the P3 component based on comparison of event-related potentials, thus making it possible to realize a device operation even when some noise is mixed.

Figure 4:
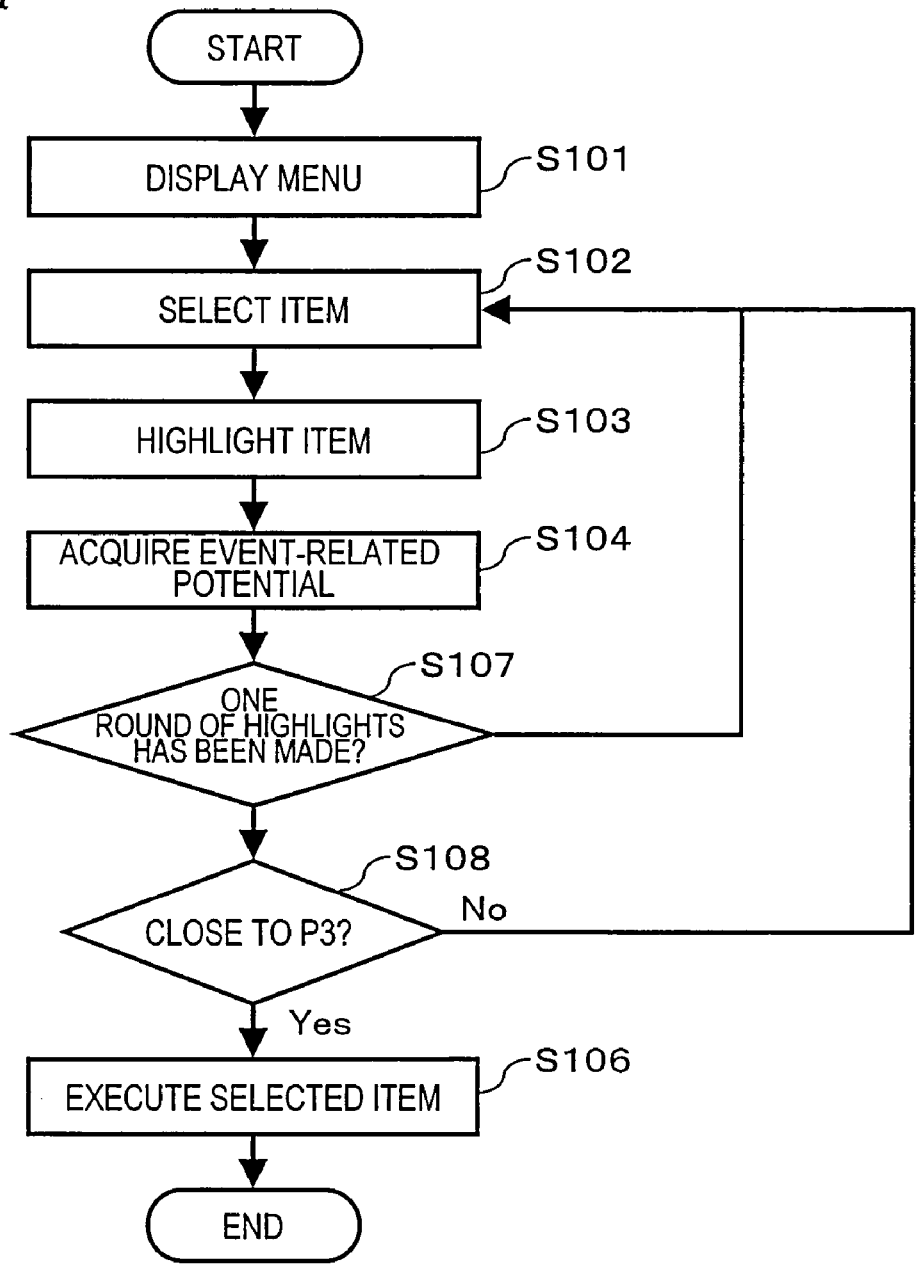
FIG. 4 A flowchart showing an example of a second usual processing procedure by an electroencephalogram interface according to the present invention (processing procedure B).

FIG. 4 shows an example of a second usual processing procedure by the electroencephalogram interface according to the present invention (processing procedure B). Note that any step where the same process as in processing procedure A of the electroencephalogram interface shown in FIG. 3 is performed is denoted by the same numeral, and the description thereof is omitted.

Step S107 branches out depending on whether or not every item for selection has been highlighted at least once. If Yes at step S107, control proceeds to step S108; if No, control returns to step S102, and the next menu item is selected.

At step S108, a possibility that the P3 component is contained in the event-related potential of each menu item acquired at step S104 is calculated; an item-by-item comparison is made; and the closest menu item is distinguished as containing the P3 component. As to the possibility that the P3 component is contained in the event-related potential of each item, the waveform whose maximum amplitude value is the largest may simply be selected as in step S104 in FIG. 3; or, the size of an average potential in a given zone may be determined, and one that has the largest average potential may be selected. Alternatively, one that has a large correlation coefficient value with respect to a template may be selected. If Yes at step S108, control proceeds to step S106; if No, control returns to step S102, and the next menu item is selected.

Thus, by comparing the event-related potential of each menu item and choosing the item having the highest possibility that the P3 component has appeared, a distinction method is realized that enables distinction even if some noise is mixed. However, when processing procedure B is used, too, a menu item that seems as if containing P3 may be selected even when the user is not looking at the menu. Therefore, again, there is a possibility that a menu item which is not intended by the user may be selected, and therefore it is preferable to perform a process having a higher distinction accuracy.

Selection of a menu item which is not intended by the user occurs all because the device is unable to determine whether the user has been looking at the menu or not. If it is possible to determine whether he or she has been looking at the menu or not, such unintended device operations can be eliminated by adjusting the distinction method, e.g., by excluding from the subject of distinction the case of not looking.

The inventors have found that, by analyzing the frequency of the electroencephalograms of a user who utilizes the electroencephalogram interface, it is possible to determine whether the user is looking at the menu or not. As a result, without newly adding a line-of-sight detection apparatus or the like, a detection that the user has not been looking at the menu can be realized. Hereinafter, an experiment performed by the inventors and the experimental results thereof will be described with reference to FIG. 5 to FIG. 7.

FIG. 5 is a diagram showing the flow of the experiment. In FIG. 5, (a) is a diagram showing the procedure of stimulation and event-related potential measurement, as a flow at the device side during the experiment. In FIG. 5, (b) is a diagram showing the procedure of tasks which are performed by the test subject during the experiment. The flows of (a) and (b) of FIG. 5 are to be performed concurrently. Based on the device operation in accordance with (a) of FIG. 5, the test subject performs an action in accordance with (b) of FIG. 5. Then, the resultant event-related potential is measured by the device in accordance with (a) of FIG. 5.

First, (a) of FIG. 5 will be described.

At step S50, the device starts electroencephalographic measurement of the test subject.

At step S51, the device presents four menu items and a selection instruction as to which menu item the test subject should select. FIG. 6(a) shows a display screen of a menu and a selection instruction which were actually presented to the test subject. In the experiment by the inventors, the indication of FIG. 6(a) was presented for 4 seconds. Hereinafter, a selected item for which a selection instruction has been issued will be referred to as a "target".

In response to this presentation, the test subject starts action. An arrow from step S51 of FIG. 5(a) to step S61 of FIG. 5(b) represents the timing at which the test subject starts action corresponding to the device operation at step S51.

At step S52, the device randomly selects a menu item.

At step S53, the menu item selected at step S52 is highlighted for 350 ms. In other words, highlighting of the menu items is switched at a switching frequency $\theta s=2.86$ Hz. FIG. 6(b) shows an example of displaying a highlighted menu item. The device counts and retains the total number of times n that the menu items have been highlighted.

At step S54, the device cuts out the electroencephalograms of a predetermined zone relative to the point of highlighting a menu item at step S53, and acquires an event-related potential. In this experiment, the event-related potential in a zone from 100 ms before highlighting to 1000 ms after highlighting was cut out.

At step S55, the device determines whether the number of times n of highlighting the menu items is no more than 40 or greater than 40. If the number of times n of highlighting is no more than 40, the device returns to the process of step S52, and repeats highlighting of the menu items. On the other hand, if the number of times n of highlighting exceeds 40, the device ends the process.

Through the above process, statistically speaking, about 10 times of highlighting is carried out for each menu item. Note that this number of times of processing was set, by experimentally taking repetitive arithmetic means of the event-related potential, as being necessary for confirming an appearance of the component. In an actual implementation as an electroencephalogram interface system, it is not always necessary to adopt such a number of times of processing.

Through step S50 to step S55 above, under conditions where the menu item to be highlighted is switched every 350 ms, the device can acquire 40 samples of the event-related potential of the test subject since highlighting as a starting point, where each menu item is highlighted about 10 times.

Next, FIG. 5(b) will be described.

At step S61, the test subject looks at the menu and selection instruction which are presented at step S51 of FIG. 5(a). Looking at selection instruction, the test subject confirms the target. This would correspond to a device operation which the user wishes to realize when actually using the electroencephalogram interface.

At step S62, the test subject watches the menu, and while looking at the menu item highlights which are presented from step S52 to S55 of FIG. 5(a), waits for the menu item which is supposed to be selected to become highlighted.

At step S63, the test subject determines whether the target was highlighted at step S61 or not. If it is determined that the target was highlighted, control proceeds to step S64; if it is determined that it was not highlighted, control returns to step S62.

At step S64, the test subject is a step of taking a mental count of the number of times that the target was highlighted. A mental count means a count of numbers taken in one's mind.

At step S65, the test subject determines whether switching of highlight is ended or not, and if the process of switching menu items by the device has been ended, ends the experiment, and if the process of switching menu items is continued, the operation from step S62 is restarted.

Note that the electroencephalograms were measured at three sites Fz, Cz, Pz (International 10-20 system) on the scalp, relative to an earlobe. The visual stimulations were presented on an 19-inch LCD display which was at 1 m in front of the test subject.

Figure 7:
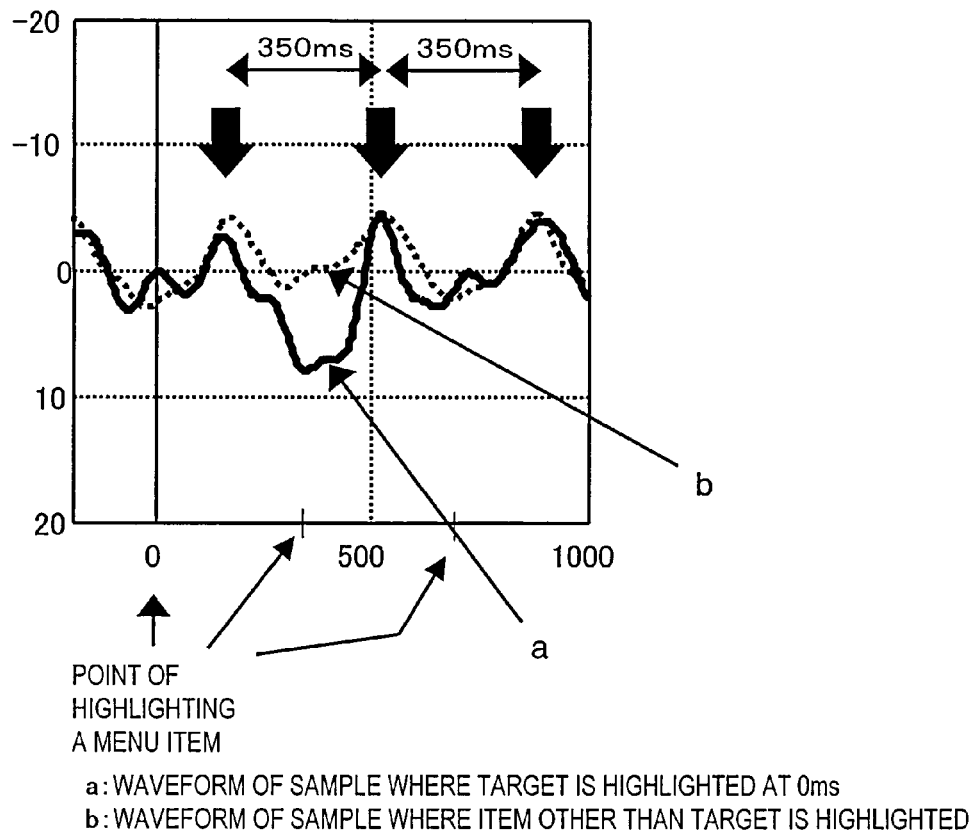
FIG. 7 A graph showing exemplary experimental results.

FIG. 7 is a graph showing exemplary experimental results. This graph represents an arithmetic mean waveform of an event-related potential measured at the electrode position Pz. A solid-line waveform a represents an arithmetic mean waveform of the event-related potential which was obtained after a target was highlighted at 0 ms. On the other hand, a dotted-line waveform b represents an arithmetic mean waveform of the event-related potential after an item other than the target was highlighted. Note that the horizontal axis of the graph is time (unit: ms), and the vertical axis is potential (unit: µV). The menu items were switched every 350 ms.

As shown by the solid-line waveform a in FIG. 7 which is associated with the target, a positive component appears 300 to 400 ms after the target is highlighted. This is a general P3 component, which is considered to coincide with the results of Non-Patent Document 1.

Furthermore, the inventors have found that a periodic feature exists commonly for the solid line and the dotted line in FIG. 7. Specifically, the inventors have found a characteristic feature in that, in both waveforms, negative extremes exist at an interval of about 350 ms. By paying attention to this characteristic feature, a frequency analysis of electroencephalograms was performed.

Figure 8:
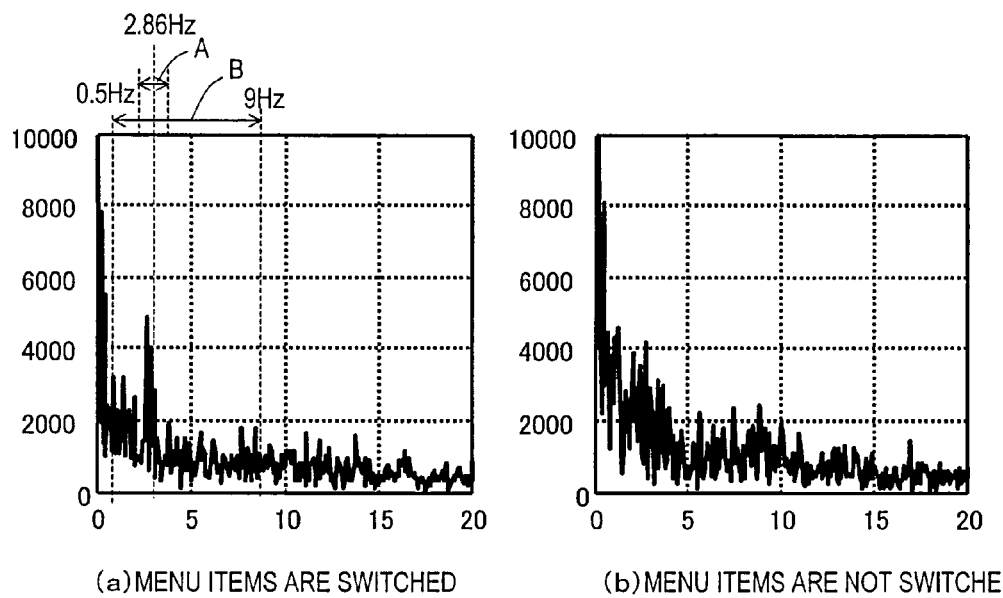
FIG. 8 (a) is a diagram showing a frequency power of electroencephalogram when menu items are highlighted while being switched every 350 ms (condition A), and (b) is a diagram showing a frequency power of electroencephalogram when a selection instruction stimulation is being presented at step S51 (condition B).

FIG. 8(a) shows a frequency power of electroencephalograms when menu items are highlighted while being switched every 350 ms (condition A), whereas FIG. 8(b) shows a frequency power of electroencephalograms when a selection instruction stimulation is being presented at step S51 (condition B). In both, the horizontal axis is frequency (unit: Hz), and the vertical axis is frequency power (unit: µV·µV/Hz).

As is clear from FIG. 8(a), it is understood that a characteristic peak exists in the frequency power under condition A. The frequency ($\theta e$) corresponding to this peak was 2.74 Hz. As described earlier, the switching frequency $\theta s$) of menu items corresponding to condition A is 2.86 Hz, which substantially matches the frequency at which the frequency power of electroencephalograms became maximal. On the other hand, according to FIG. 8(b), no characteristic peaks exist in the frequency power under condition B.

Taking these into consideration, it is presumable that the switching frequency ($\theta s$) of menu item highlights influenced the frequency of electroencephalograms, thus causing periodic changes in the event-related potential. Therefore, by calculating the frequency ($\theta e$) at which the frequency power of electroencephalograms becomes maximal, it becomes possible to determine whether the user has been looking at the menu or not.

Incidentally, it is known that when a visual stimulation which flickers at the same position is presented, a component called SSVEP appears in the electroencephalograms in synchronization with the flickering of the visual stimulation (Xiaorong Gao et al., A BCI-Based Environmental Controller for the Motion-Disabled, IEEE Transactions on Neural Systems and Rehabilitation Engineering, 2003).

However, the inventors believe that the results obtained from experiment of the inventors are different from SSVEP. The reason is that the visual stimulation in the present experiment is switching of highlights, which does not flicker at the same position. Another reason is that, in the present experiment, the test subject is in a state of waiting for a relevant menu item (target) to be highlighted, which is different from a state of merely looking at a flickering stimulation as in the SSVEP experiments. In other words, experiment of the inventors and the SSVEP experiments are based on different settings.

Next, a distinction necessity determination apparatus according to an embodiment of the present invention will be described in detail. As a representative frequency ($\theta e$), the distinction necessity determination apparatus calculates a frequency at which the frequency power of the user electroencephalograms becomes maximal during use of the electroencephalogram interface. Then, based on a relative quantity between the representative frequency ($\theta e$) and the switching frequency of menu items, it is determined whether the representative frequency ($\theta e$) is related to the switching of menu items or not. "Based on a relative quantity" means: depending on whether a difference between the frequency ($\theta e$) and the switching frequency of menu items, or a ratio between the frequency ($\theta e$) and the switching frequency of menu items, is no greater than a threshold value or greater than the threshold value, for example.

If it is equal to or smaller than the threshold value, it is determined that the representative frequency ($\theta e$) and the switching frequency of menu items are related, i.e., the user has been looking at the menu. As a result, the electroencephalogram signal is adopted as the subject of distinction by the electroencephalogram interface.

On the other hand, if it is greater than the threshold value, it is determined that the representative frequency ($\theta e$) and the switching frequency of menu items are not related and that the user has not been looking at the menu. As a result, the electroencephalogram signal is excluded from the subject of distinction by the electroencephalogram interface. This makes it possible to reduce device operations which are not intended by the user.

Embodiment 1

Figure 9:
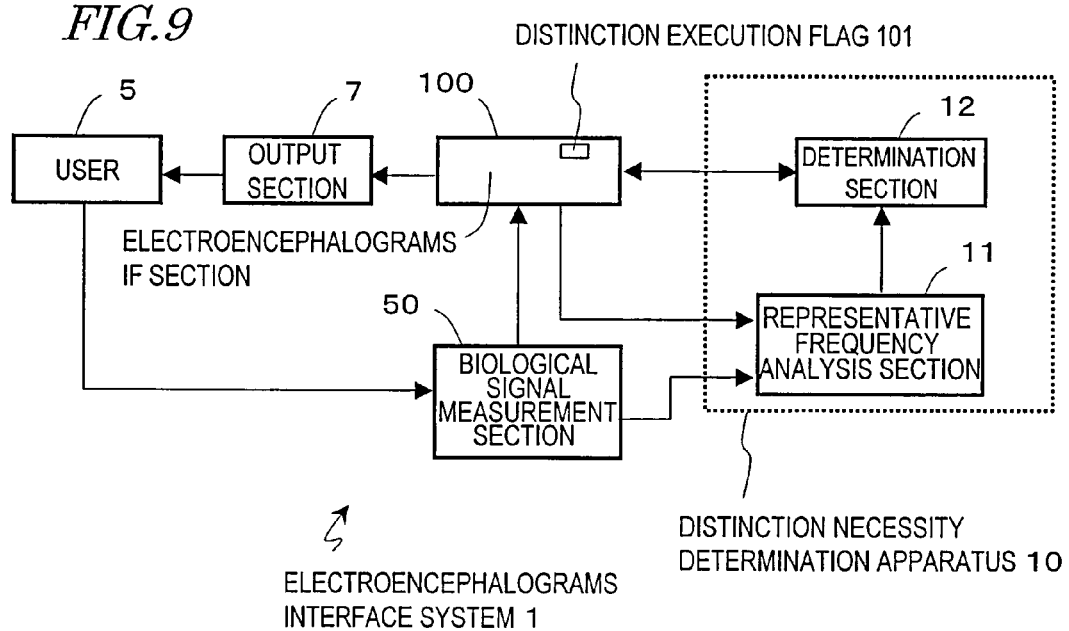
FIG. 9 A diagram showing a functional block construction of the electroencephalogram interface system 1 according to Embodiment 1 of the present invention.

FIG. 9 shows a functional block construction of the electroencephalogram interface system 1 according to the present embodiment. The electroencephalogram interface system 1 includes an output section 7, a distinction necessity determination apparatus 10, a biological signal measurement section 50, and an electroencephalogram interface (IF) section 100. FIG. 9 also shows functional blocks of the distinction necessity determination apparatus 10 (hereinafter referred to as "determination apparatus 10"). The user 5 block is illustrated for convenience of explanation. The output section 7 presents a screen on which a menu and the like are presented to the user 5.

The user 5 is merely carefully looking, as to whether a menu item concerning a device manipulation which is presented by the electroencephalogram interface section 100 on the output section 7 is highlighted or not, and does not make any manipulation input. However, the device operates in accordance with the menu item which is selected via the electroencephalogram interface section 100.

The determination apparatus 10 is connected to the biological signal measurement section 50 and the electroencephalogram interface section 100 in a wireless or wired manner, and performs transmission and reception of signals. Although FIG. 9 illustrates the biological signal measurement section 50 and the electroencephalogram interface section 100 as separate entities from the determination apparatus 10, this is only exemplary. A part or whole of the biological signal measurement section 50 and the electroencephalogram interface section may be provided within the determination apparatus 10.

The biological signal measurement section 50 is an electroencephalograph which detects a biological signal of the user 5, and measures electroencephalograms as a biological signal. The electroencephalograph may a head-mounted electroencephalograph as shown in FIG. 1. It is assumed that the user 5 has put on the electroencephalograph in advance.

Electrodes are disposed on the biological signal measurement section 50 so that, when worn on the head of the user 5, the electrodes come into contact with the head at predetermined positions. The positioning of the electrodes may be, for example, Pz (median parietal), A1 (earlobe), and the nasion of the user 5. However, it will suffice if there are at least two electrodes, and potential measurement will be possible with only Pz and A1, for example. These electrode positions are to be determined based on reliability of signal measurements, wearing ease, and the like.

Thus, the biological signal measurement section 50 is able to measure the event-related potential of the user 5. The measured electroencephalograms of the user 5 are sampled so as to be computer-processible, and are sent to the electroencephalogram interface section 100 and the determination apparatus 10. Note that, in order to reduce the influence of noises which may be mixed in the electroencephalograms, the electroencephalograms to be measured in the biological signal measurement section 50 are subjected to band-pass filtering from e.g. 0.05 to 20 Hz in advance, and to baseline correction with respect to an average potential at e.g. 100 milliseconds before highlighting of menu items.

The electroencephalogram interface section 100 presents menu items concerning device manipulations to the user, cuts out the electroencephalograms measured by the biological signal measurement section 50, and subjects it to distinction. Then, it controls the device operation according to the distinction result. The basic operation of the electroencephalogram interface section 100 is as described above.

Assuming that the device to be controlled by using the electroencephalogram interface section 100 is the TV 2 shown in FIG. 1, for example, the menu is presented to the user 5 via the output section 7. As shown in FIG. 2(a), the menu items are highlighted with a predetermined switching period, one in every $\theta s$ (e.g. 2.86 Hz). $\theta s$ may be 2 Hz, 3 Hz, or 5 Hz.

The electroencephalogram interface section 100 retains a distinction execution flag 101.

The distinction execution flag 101 is referred to in order to determine whether or not to distinguish a characteristic feature of the event-related potential contained in the electroencephalograms of the user 5 measured by the biological signal measurement section 50. For example, when the distinction execution flag 101 is "1", the electroencephalogram interface section 100 adopts as the subject of distinction the event-related potential which has been obtained. On the other hand, when the distinction execution flag 101 is "0", the electroencephalogram interface section 100 excludes from the subject of distinction the event-related potential which has been obtained. By a method described later, the distinction execution flag 101 is set based on an instruction from the determination apparatus 10. Note that the operations corresponding to the respective values of "0" and "1" are examples, and other examples may be adopted.

When the distinction execution flag 101 is set to "1", from the electroencephalograms of the user 5 measured by the biological signal measurement section 50, the electroencephalogram interface section 100 cuts out e.g. 500 ms since the point of highlighting the menu item as a starting point, which is longer than the peak latency of the P3 component, and distinguishes the waveform. The time for which to cut out the electroencephalograms may be 1000 ms in order to account for a return from a peak of the waveform. The method of distinguishing the event-related potential may be to simply subject the waveform to threshold processing, or as described in Patent Document 2, a correlation coefficient may be calculated with respect to a template which is generated from an arithmetic mean waveform of the P3 component that has been measured with respect to each user in advance.

Next, the detailed construction of the determination apparatus 10 of the present embodiment will be described. One main feature of the present invention lies in the construction and operation of the determination apparatus 10.

The determination apparatus 10 includes a representative frequency analysis section 11 and a determination section 12.

The representative frequency analysis section 11 calculates a frequency (representative frequency ($\theta e$)) at which the frequency power has a characteristic peak, and sends the frequency to the determination section 12. Hereinafter, a method of calculating the representative frequency ($\theta e$) will be specifically described.

First, the representative frequency analysis section 11 calculates a frequency power of the electroencephalograms of the user 5 measured by the biological signal measurement section 50 by e.g. fast Fourier transform (Fast Fourier Transform; FFT). The representative frequency analysis section 11 may calculate the frequency power by cutting out the electroencephalogram of e.g. about 1 second before and after the timing at which the electroencephalogram interface section 100 highlights the menu item. Note that the length of the time window for which to cut out the electroencephalograms may be varied according to the switching frequency of highlighting. In order to improve the accuracy of frequency analysis, the length of the time window may be set so that two or more times of highlighting occurs.

Next, out of the calculated frequency power, the representative frequency analysis section 11 determines a representative frequency ($\theta e$) from a local maximum of frequency power.

The range in which to determine a local maximum of frequency power may be a range in which the influences of DC components and spontaneous electroencephalograms such as alpha waves (frequency band of 1 Hz to 8 Hz or a broader frequency band of 0.5 Hz to 9 Hz) are small, for example. Alternatively, the switching frequency of menu item highlights may be acquired from the electroencephalogram interface section 100, and a frequency power in the neighborhood of that frequency may be used for the determination. FIG. 8(a) shows a frequency band A in the neighborhood ±0.2 Hz from the switching frequency of menu item highlights and a frequency band B of 0.5 Hz to 9 Hz.

As a local maximum of frequency power, the largest one among all local maximums within the aforementioned range may be selected, for example. Furthermore, a threshold value for frequency power may be set (e.g. a frequency power of 4000 ($\mu V \cdot \mu V/Hz$)), and a condition of being equal to or greater than the threshold value may be imposed. Since the representative frequency analysis section 11 is able to identify a characteristic peak as a local maximum of frequency power, a frequency corresponding to that local maximum can be adopted as the representative frequency ($\theta e$).

Note that the local maximum of frequency power being determined in a frequency band from 0.5 Hz to 9 Hz means that the switching frequency ($\theta s$) of menu item highlights may be selected from 0.5 Hz to 9 Hz, that is, the switching frequency ($\theta s$) being variable. The switching would be very slow at 0.5 Hz, whereas the switching would be very fast at 9 Hz. Depending on the gender, age, proficiency, etc., of the user 5, practical use may not be possible unless the switching of menu item highlights is slow, or it may still be sufficiently possible even if the switching of menu item highlights is fast. For this reason, it was ensured that the switching frequency ($\theta s$) of menu item highlights is selectable in the frequency band from 0.5 Hz to 9 Hz, and also that the local maximum of frequency power is to be determined in the frequency band from 0.5 Hz to 9 Hz.

Note that the period of menu item highlights becomes certain when the electroencephalogram IF section 100 has performed about two times of menu item highlighting, so that a significant difference will appear in the local maximum of frequency power.

The determination section 12 calculates a relative quantity (a difference or ratio) between the representative frequency ($\theta e$) received from the representative frequency analysis section 11 and the menu item switching frequency ($\theta s$) received from the electroencephalogram interface section 100, and determines whether the two are interrelated or not. The determination as to whether the two are interrelated may be made, based on a frequency analysis accuracy which is determined by the sampling frequency and the time window for frequency analysis, depending on whether the difference between $\theta s$ and $\theta e$ is no more than 0.2 Hz, or whether the ratio between $\theta s$ and $\theta e$ is within the range of no less than 0.93 and no more than 1.07, for example. In the following description, it is assumed that a difference is utilized for determination. Note that the threshold value may be a variable instead of a fixed value.

If it is determined that the two are interrelated, the determination section 12 does not perform anything. On the other hand, if it is determined the two are not interrelated, the determination section 12 adjusts the electroencephalogram distinction method in the electroencephalogram interface section 100, because it is presumable that the user 5 is not looking at the menu.

An adjustment of the electroencephalogram distinction method is to, for example, give an instruction that the distinction execution flag 101 retained in the electroencephalogram interface section 100 be set to the value "0", which indicates exclusion from the subject of distinction. Although the above description assumes that the determination section 12 does not perform anything when determining that the above two are interrelated, an instruction to set the distinction execution flag 101 to "1" may be given instead, in order to allow adoption as the subject of distinction, for example.

Based on such a construction, it becomes possible to determine whether the user 5 has been looking at highlighting of the menu items, by using the frequency ($\theta e$) of the electroencephalograms as an index. This makes it possible to make an adjustment for the distinction method by causing any sample where the user 5 is not looking at the menu to be excluded from the subject of distinction. As a result, the device operations that are not intended by the user 5 are reduced, whereby an electroencephalogram interface which is easy for the user 5 to use can be realized.

Next, with reference to the flowchart of FIG. 10, an overall processing procedure which is performed in the electroencephalogram interface system 1 of FIG. 9 will be described.

Figure 10:
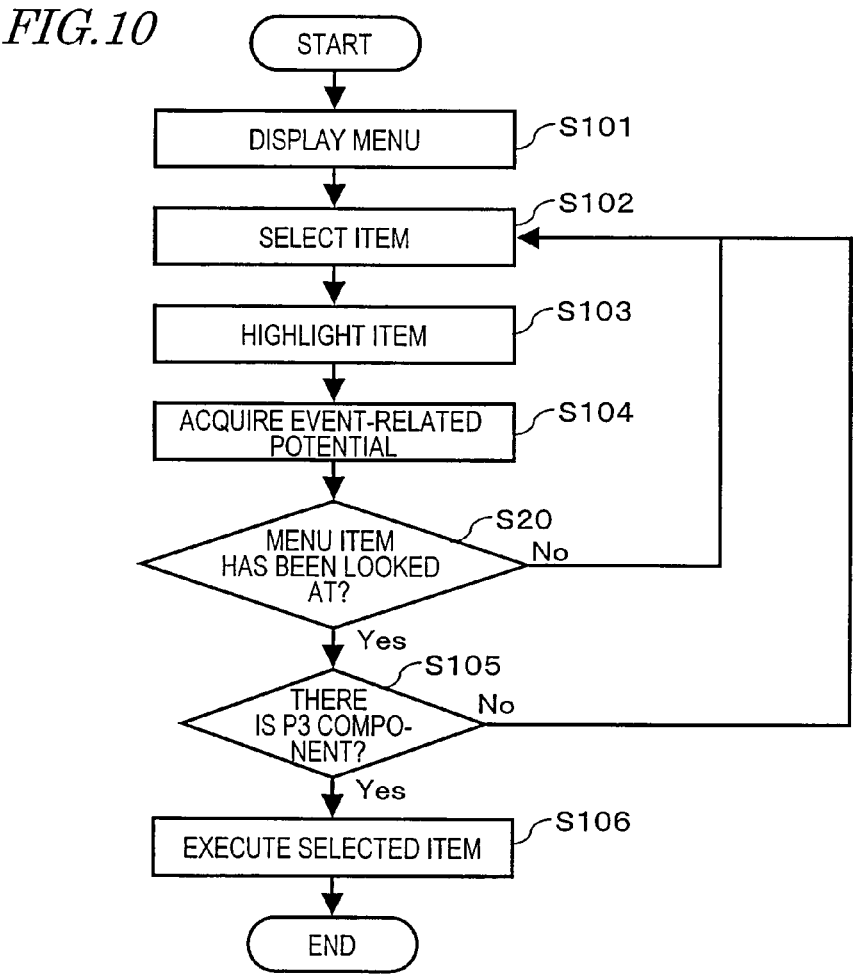
FIG. 10 A flowchart showing a processing procedure by the electroencephalogram interface system 1 according to Embodiment 1.

FIG. 10 shows a processing procedure by the electroencephalogram interface system 1 of the present embodiment. The electroencephalogram interface system 1 has a function of determining whether the user 5 is looking at the menu or not, and excluding from the subject of distinction the case of not looking at the menu.

Note that step S101 to step S106 shown in FIG. 10 are identical with the processing procedure by the electroencephalogram interface shown in FIG. 3. Therefore, the description thereof will be omitted hereinafter.

The difference from the processing procedure by the electroencephalogram interface of FIG. 3 is that step S20 of determining whether the user 5 has been looking at highlighting of menu items or not is provided.

At step S20, from the frequency of the electroencephalogram of the user 5 measured by the biological signal measurement section 50, the determination apparatus 10 determines whether the user 5 has been looking at highlighting of menu items or not. The specific process will be described later with reference to FIG. 11.

If the determination apparatus 10 determines that the user 5 has been looking at the menu (Yes at step S20), the process proceeds to step S105. At step S105, the electroencephalogram IF section 100 performs a distinction as to whether the P3 component appears in the event-related potential measured at the step S104.

On the other hand, if the determination apparatus 10 determines that the user 5 has not been looking at the menu (No at step S20), the electroencephalogram IF section 100 does not perform a distinction process for the event-related potential, and control returns to the process of step S102. Then, for a next menu item highlight, the electroencephalogram IF section 100 selects an item to be highlighted.

Next, with reference to FIG. 11, the detailed processing of step S20 will be described.

FIG. 11 shows a detailed procedure of the process of determining whether the user 5 has been looking at a menu item or not. This process is performed by the representative frequency analysis section 11 and the determination section 12 composing the determination apparatus 10.

At step S21, the representative frequency analysis section 11 cuts out the electroencephalograms of the user 5 measured by the biological signal measurement section 50. The timing of cutting out the electroencephalograms may be a point in time at which the electroencephalogram interface section 100 presents the menu, for example, or may be independently decided by the representative frequency analysis section 11, e.g. every 1 second. The zone in which to cut out the electroencephalograms may be e.g. 1 second long, 2 seconds long, 3 seconds long, or 5 seconds long.

At step S22, the representative frequency analysis section calculates a frequency power of the electroencephalograms of the user 5 cut out at step S21 by fast Fourier transform FFT.

At step S23, the representative frequency analysis section 11 selects a frequency at which the frequency power calculated at step S22 becomes maximal as a representative frequency ($\theta e$), and sends it to the determination section 12.

At step S24, the determination section 12 receives the switching frequency ($\theta s$) of menu item highlights from the electroencephalogram interface section 100, and calculates a difference between $\theta e$ and $\theta s$.

At step S25, the determination section 12 calculates a difference between $\theta s$ and $\theta e$, and determines whether the difference is smaller than a threshold value or not. If the difference is smaller than the threshold, value control proceeds to step S26; if it is equal to or greater than the threshold value, control proceeds to step S27.

At step S26, the determination section 12 determines that the user 5 has been looking at the menu, and performs nothing for the electroencephalogram IF section 100. Alternatively, the determination section 12 may instruct the electroencephalogram IF section 100 to set the distinction execution flag 101 retained by the electroencephalogram IF section 100 to "1".

On the other hand, at step S27, the determination section 12 determines that the user 5 is not looking at the menu, and instructs the electroencephalogram IF section 100 to set the distinction execution flag 101 to "0".

Such processing precludes execution of the distinction process when the user is not looking at the menu, which would cause a decrease in the distinction ratio, and a reduction in the device operations that are not intended by the user can be realized.

In the present embodiment, when the user is not looking at the menu, this electroencephalogram signal is excluded from the subject of distinction. Alternatively, when the user is not looking at the menu, the device may be allowed to operate so that its operating state is set back by one or more. In that case, device operations that are not intended by the user can be canceled as the user merely moves his or her gaze off the menu, whereby the manipulability of the electroencephalogram interface is significantly improved.

Moreover, it becomes unnecessary to provide "RETURN" as a menu item, and therefore another menu item can be provided instead. Furthermore, a video or audio alert may be presented when the user is not looking at the menu items, for example. Thus, the ability to detect not looking at the menu makes possible various device operations.

By providing the determination apparatus 10 in the electroencephalogram interface system 1 of the present embodiment, it becomes possible to determine whether the user 5 has been looking at highlighting of menu items, from the frequency of the electroencephalograms of the user 5 using the electroencephalogram interface. This makes possible an adjustment of the distinction method by causing any case of not looking at the menu to be excluded from the subject of distinction. Thus, a reduction in the device operations that are not intended by the user can be realized, and therefore an interface which is easy to use can be realized.

Embodiment 2

In the electroencephalogram interface system 1 of Embodiment 1, with respect to one kind of menu (having a plurality of menu items) that is presented by the electroencephalogram interface section 100, it is determined whether the user is looking at the menu items or not from a characteristic feature of the frequency of the user electroencephalogram when using the electroencephalogram interface system, and the case where he or she is not looking at the menu item is excluded from the subject of distinction, thereby realizing a reduction in the device operations that are not intended by the user.

In the above-described electroencephalogram interface, the time until a menu item to be selected becomes highlighted will increase in proportion with the number of menu items because menu items are randomly highlighted. Therefore, the number of menu items must be limited in consideration of manipulability.

Therefore, in situations where a display apparatus with a large image displayable region can be used, e.g. a large-screen television set which is gaining prevalence in the recent years, a plurality of menus may be simultaneously presented at different positions, whereby it becomes possible to select a menu item from among the large number of menu items in a short time.

When a plurality of menus are simultaneously presented on one screen, menu items are highlighted in each menu. Therefore, in effect, a plurality of menu items will be highlighted at the same point in time. Hence, it is necessary to first identify which menu is being looked at by the user, and then a device operation that is intended by the user must be uniquely determined.

In the electroencephalogram interface system of the present embodiment, a switching frequency of menu item highlighting is independently set for each of the plurality of menus, and highlighting of each plurality of menu items is switched. Then, based on a characteristic feature of the frequency of the user electroencephalograms, a determination is made as to which menu is being looked at by the user. As a result, even in a situation where a plurality of menus are simultaneously presented and a plurality of menu items are being highlighted at the same point in time, it is possible to identify which menu is being looked at by the user. Then, it can be determined which menu item execution is being desired of by the user, with respect to the identified menu, based on the event-related potential. As a result, a highly accurate distinction can be realized.

FIG. 12 shows a functional block construction of the electroencephalogram interface system 2 of the present embodiment. FIG. 12 also shows functional blocks of a distinction necessity determination apparatus 20. The user 5 block is illustrated for convenience of explanation.

Figure 13:
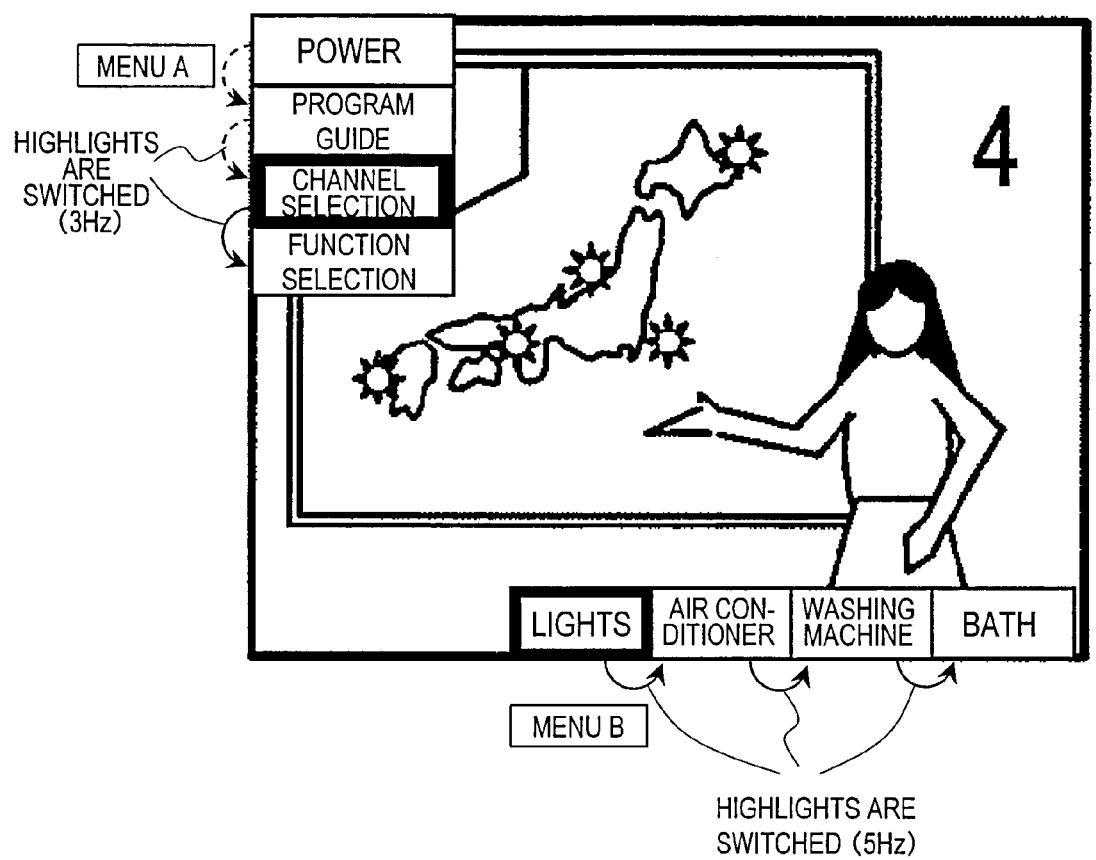
FIG. 13 A diagram showing an example where two kinds of menus are being presented on a large-screen television set by using the electroencephalogram interface system 2.

Furthermore, FIG. 13 shows a manner in which electroencephalogram interface system 2 of the present embodiment is used. Specifically, FIG. 13 illustrates an example where two kinds of menus are presented on a large-screen television set by using the electroencephalogram interface system 2.

For ease of understanding, the displaying example shown in FIG. 13 will be first described. FIG. 13 presents menu A, which concerns TV manipulations, and menu B, which concerns manipulations of devices other than TV. "Channel selection" is highlighted in menu A, whereas "lights" are highlighted in menu B. In this example, switching of highlights is performed at 3 Hz for menu A, and at 5 Hz for menu B. In a situation where the user is looking at menu A, a representative frequency ($\theta e$) which is relatively close to 3 Hz is observed, whereas in a situation where the user is looking at menu B, a representative frequency ($\theta e$) which is relatively close to 5 Hz is observed. In the case where the user is looking at neither menu, no representative frequency ($\theta e$) is observed. By presenting a plurality of menus by using the electroencephalogram interface in the above manner, it becomes possible to manipulate a plurality of devices with ease and certainty.

The electroencephalogram interface system 2 differs from the electroencephalogram interface system 1 (FIG. 9) of Embodiment 1 in that: a plural-menu presenting electroencephalogram interface section 200 is comprised instead of the electroencephalogram interface section 100 of Embodiment 1; and in the construction of the distinction necessity determination apparatus 20 (hereinafter referred to as "determination apparatus 20"), the determination section 12 is replaced by a distinction subject determination section 21. Note that, among the component elements of the electroencephalogram interface system 2, component elements which are identical to those of the electroencephalogram interface system 1 (FIG. 9) will be denoted by like reference numerals and the descriptions thereof will be omitted.

The plural-menu presenting electroencephalogram interface section 200 (hereinafter referred to as "electroencephalogram IF section 200") expands the functions of the electroencephalogram interface section 100 so as to simultaneously present a plurality of menus, and permits a function to be executed from a menu item of each menu.

The electroencephalogram IF section 200 presents a plurality of menus to the user 5 via the output section 7. For example, in one menu, the electroencephalogram IF section 200 may display menu items concerning detailed functions of a specific device, and in another menu, display menu items concerning a plurality of devices that are capable of being controlled. Then, by setting the switching frequency ($\theta s$) of menu item highlights of each menu to a different value, highlighting is switched.

In the example shown in FIG. 13, $\theta sa$ is set to 3 Hz and $\theta sb$ is set to 5 Hz, where $\theta sa$ and $\theta sb$ are the highlight frequencies of menu A and menu B, respectively. The frequencies ($\theta s$) of menu item highlights only need to be in a range where the user 5 is able to recognize highlights. Moreover, in consideration of the influence of multiple frequency components, it is preferable to set $\theta sa$ and $\theta sb$ so as to not to be integer multiples. Moreover, the timing of highlighting menu items may be set so as not to overlap.

Moreover, the electroencephalogram IF section 200 retains a distinction execution flag group 201. The distinction execution flag group 201 is a collection of a plurality of distinction execution flags. In the present embodiment, it is assumed that the distinction execution flags are provided corresponding to the menus. For example, the first bit of the distinction execution flag group 201 corresponds to menu A, whereas the second bit corresponds to menu B. When "1" is set to either flag value, the electroencephalogram IF section 200 adopts as the subject of distinction the event-related potential which is being obtained. Then, based on that event-related potential, it makes a determination as to the manipulation indicated in which menu item of the menu corresponding to the flag value "1" is to be executed, and executes an operation corresponding to that item. The distinction execution flag group 201 is updated by the distinction subject determination section 21 described next.

The distinction subject determination section 21 (hereinafter referred to as "determination section 21") makes a comparison between the switching frequencies ($\theta sa$, $\theta sb$) received from the electroencephalogram IF section 200 and the representative frequency ($\theta e$) received from the representative frequency analysis section 11 at which the electroencephalogram frequency power of the user 5 becomes maximal, and determines which menu is being looked at by the user 5.

As is done by the determination section 12 of Embodiment 1, the determination may be made by calculating a relative quantity (a difference or ratio) between the representative frequency ($\theta e$) and each menu item switching frequency ($\theta sa$, $\theta sb$) and based on that relative quantity. For instance, in an exemplary case where a difference is utilized as the relative quantity, the differences between the representative frequency ($\theta e$) and the respective switching frequencies ($\theta sa$, $\theta sb$) may be compared, and the menu with a smaller difference may be determined as having been looked at. Alternatively, assuming a threshold value of 0.2 Hz, the menu whose difference between the representative frequency ($\theta e$) and each switching frequency ($\theta sa$, $\theta sb$) is equal to or smaller than the threshold value may be determined as having been looked at, and otherwise it may be determined that neither menu has been looked at.

Depending on the determination result, in the distinction execution flag group 201 provided in the electroencephalogram IF section 200, the determination section 21 instructs the electroencephalogram IF section 200 to set the value of the distinction execution flag corresponding to the menu which has been looked at by the user 5 to "1". In the case where the user 5 has been looking at neither menu, the determination section 21 gives no instruction to the electroencephalogram IF section 200, or gives an instruction that all flag values in the distinction execution flag group 201 be set to "0". This enables sure exclusion from the subject of distinction, whereby erroneous recognitions can be reduced.

Upon receiving the determination result by the determination section 21, the electroencephalogram IF section 200 distinguishes the event-related potential related to menu item highlights of the corresponding menu, and if it is determined that the P3 component exists, executes a device operation of the corresponding menu item.

Thus, when a plurality of menus are simultaneously presented and the menu items are highlighted at respectively different frequencies, it becomes possible to determine which menu has been looked at by the user. This enables a distinction that is limited to the menu items of a menu which has been looked at by the user, whereby distinction accuracy is improved. As a result, it is possible to select a menu item from among a large number of menu items in a short time.

Next, with reference to the flowchart of FIG. 14, the overall processing procedure performed by the electroencephalogram interface system 2 will be described.

Figure 14:
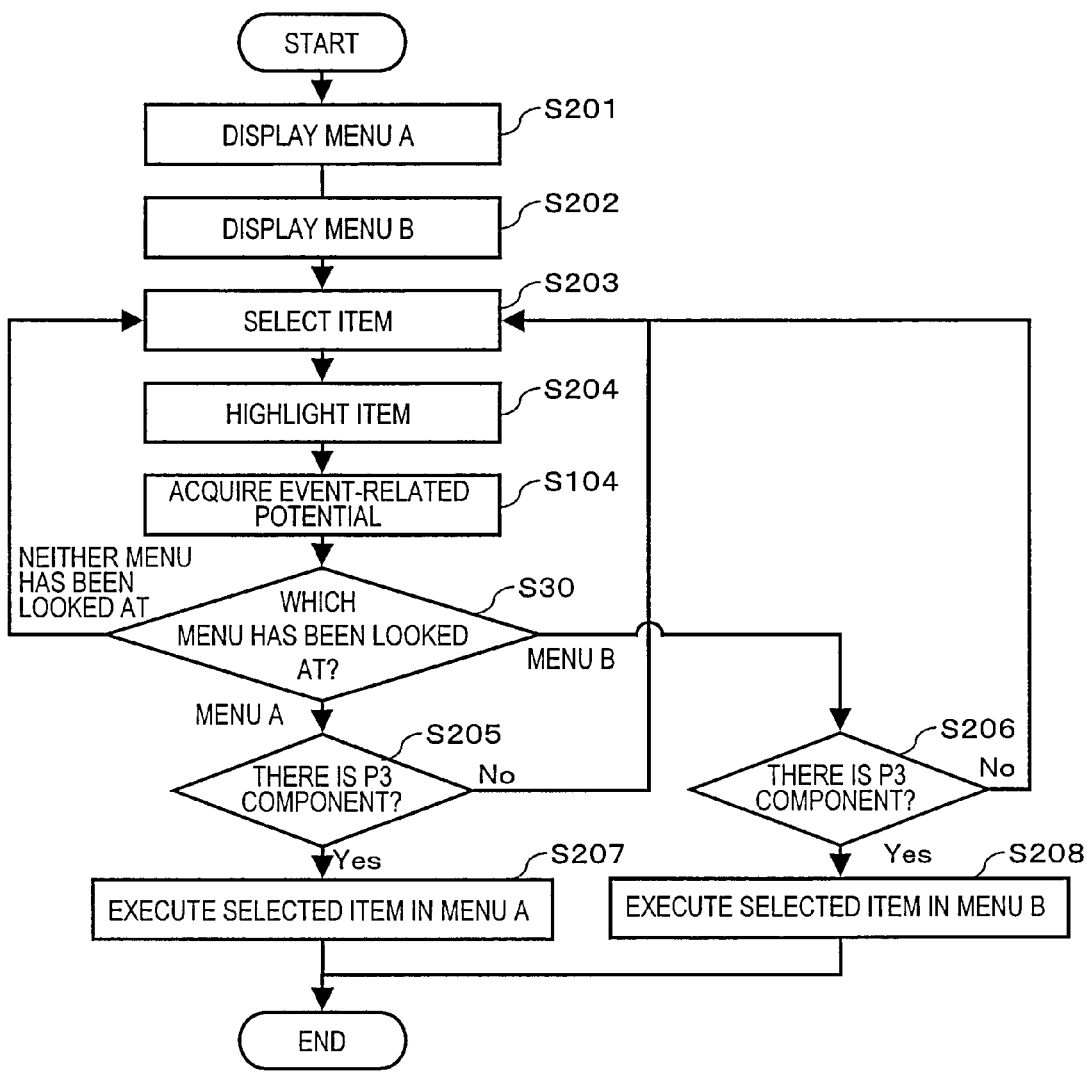
FIG. 14 A flowchart showing a processing procedure by the electroencephalogram interface system 2 according to Embodiment 2.

FIG. 14 shows a processing procedure by the electroencephalogram interface system 2 of the present embodiment. As an instance of plural menus, FIG. 14 shows a processing procedure in the case of presenting two kinds of menus menu A and menu B as shown in FIG. 13. It is assumed that menu A and menu B are each composed of a few menu items. See the displaying example shown in FIG. 13 for example. Any step where the same process as in the processing by the electroencephalogram interface system 1 (FIG. 10) is performed is denoted by the same reference numeral, and the description thereof is omitted.

At step S201, the electroencephalogram IF section 200 presents menu A to the user 5.

At step S202, the electroencephalogram IF section presents menu B to the user 5. Note that step S201 and step S202 may be simultaneous, or at separate points in time.

At step S203, the electroencephalogram IF section selects a menu item to be highlighted from menu A or menu B. The decision as to from which menu a menu item is to be selected is based on an order that is determined by each frequency of menu item highlighting.

At step S204, the electroencephalogram IF section highlights the menu item selected at step S203. The timing of highlighting the menu item is determined based on each frequency of menu item highlighting.

At step S30, the determination apparatus 20 determines which menu has been looked at by the user 5, or else that neither menu has been looked at, and control branches out. The details of the process of step S30 will be described later.

At step S205, the electroencephalogram IF section 200 makes a distinction as to whether or not the P3 component is contained in the event-related potential since menu item highlighting of menu A measured at step S104 as a starting point. The method of distinguishing the P3 component may be to simply subject the waveform to threshold processing, or as described in Patent Document 2, a correlation coefficient may be calculated with respect to a template which is generated from an arithmetic mean waveform of the P3 component that has been measured with respect to each user in advance. If Yes at step S205, control proceeds to step S207; if No, control returns to step S203 and the next menu item is selected.

At step S206, the electroencephalogram IF section 200 makes a distinction as to whether the P3 component is contained in the event-related potential since menu item highlighting of menu B measured at step S104 as a starting point. The distinction of the P3 component is similar to step S205. If Yes at step S206, control proceeds to step S208; if No, control returns to step S203 and the next menu item is selected.

At step S207, the electroencephalogram IF section 200 executes a process corresponding to the menu item in menu A that is selected at step S205. As a result, this menu item is selected and executed.

At step S208, the electroencephalogram IF section 200 executes a process corresponding to the menu item in menu B that is selected at step S206. As a result, this menu item is selected and executed.

Next, with reference to FIG. 15, detailed processing of step S20 will be described.

Figure 15:
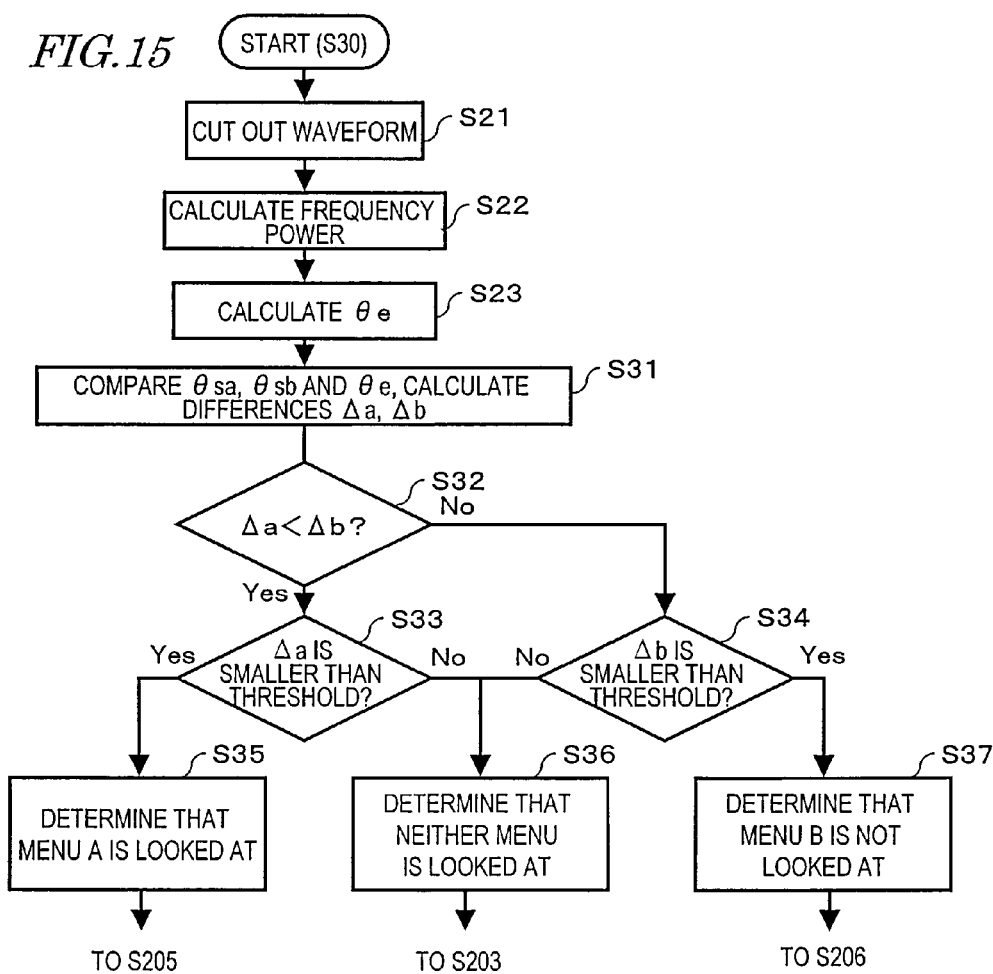
FIG. 15 A flowchart showing a detailed procedure of a process of determining whether the user 5 has been looking at menu A or menu B, or not looking at either menu.

FIG. 15 shows a detailed procedure of the process of determining which one of menu A and menu B has been looked at by the user 5, or else that neither menu has been looked at. This process is performed by the representative frequency analysis section 11 and the determination section 21 composing the determination apparatus 20. In the process of FIG. 15, an example will be illustrated where a difference is utilized as a relative quantity between the representative frequency (θe) and each highlight switching frequency (θsa, θsb). Any step concerning the same process as in the processing shown in FIG. 11 is performed is denoted by the same reference numeral, and the description thereof is omitted.

At step S31, the determination section 21 makes a comparison between: the highlight switching frequency (θsa) of menu A and the highlight switching frequency (θsb) of menu B received from the electroencephalogram IF section 200; and the representative frequency (θe) of a frequency power maximal of the electroencephalograms of the user 5 received at step S23 from the representative frequency analysis section 11, and calculates differences Δa and Δb.

At step S32, the determination section 21 determines the sizes of Δa and Δb calculated at step S31. If Δa is smaller (Yes at step S32), the process proceeds to step S33; if Δb is smaller (No at step S32), the process proceeds to step S34. Note that, in the case of making a two-state determination of which one of menu A and menu B has been looked at, a comparison between Δa and Δb may be made and the smaller menu may be determined as having been looked at, and therefore the process of S33 to S37 below is unnecessary.

At step S33, control of the determination section 21 branches out depending on whether Δa is smaller than a threshold value or not. If the difference is equal to or smaller than the threshold value, the process proceeds to step S35; if it is equal to or greater than the threshold value, the process proceeds to step S36. The threshold value may be e.g. 0.1 Hz, or may be 0.2 Hz or 0.3 Hz.

At step S34, the determination section 21 determines whether Δb is smaller than the threshold value or not, and control branches out. If the difference is equal to or smaller than the threshold value, control proceeds to step S37 as Yes; if it is equal to or greater than the threshold value, control proceeds to S36 as No. The threshold value may be determined as in step S33.

At step S35 or step S37, the determination section 21 determines that menu A is being looked at or menu B is being looked at, respectively. At step S36, it is determined that neither menu is being looked at.

Through such processing, a plurality of menu items having independent highlighting switching frequencies are presented simultaneously, and a determination is made as to which menu is being looked at by the user, based on the frequency of the user electroencephalograms. As a result, a highly accurate distinction can be realized even in a situation where a plurality of menu items are simultaneously presented, e.g. when a plurality of devices are to be manipulated.

By providing the determination apparatus 20 in the electroencephalogram interface system 2 of the present embodiment, it becomes possible to determine which menu has been looked at by the user 5, from the frequency of the electroencephalograms of the user 5 using the electroencephalogram interface. As a result, even in a situation where a plurality of menu items are simultaneously presented, it is possible to adjust the distinction method for each menu. Thus, it is possible to select a menu item from among a large number of menu items in a short time, and an electroencephalogram interface which is easy to use can be realized.

In the above embodiments, the determination sections 12 and 21 indirectly control the electroencephalogram interface sections 100 and 200 by utilizing distinction execution flags. However, without utilizing distinction execution flags, the determination sections 12 and 21 may directly instruct the electroencephalogram interface sections 100 and 200 to perform operations corresponding to the flag values "0" and "1".

Embodiment 3

In the electroencephalogram interface system 1 of Embodiment 1, from the frequency of the electroencephalograms of a user in a predetermined time window during use of the electroencephalogram interface system, the distinction method adjustment apparatus 10 determines whether the user has been looking at a menu item or not, and excludes from the subject of distinction the case where he or she is not looking at the menu item, whereby a reduction in the device operations that are not intended by the user is realized.

However, especially when the length of the time window is not sufficient, representative frequency is susceptible to the influences of background electroencephalograms and electrooculær or myoelectric noises. For example, even if the user is looking at the highlights, there is a possibility of erroneously determining that the user is not looking at the highlights. Since Embodiment 1 employs the representative frequency as an absolute index and determines the necessity of distinction in terms of "1" or "0", correct distinction is not possible in the case of erroneous determinations.

Therefore, in the electroencephalogram interface system of the present embodiment, a distinction parameter for the P3 component after highlighting is adjusted based on the representative frequency. This restores the possibility of detecting the user's intent of selection based on the P3 component after highlighting, even if an erroneous determination is made as to whether highlights have been looked at or not, so that a more accurate distinction can be realized.

Figure 16:
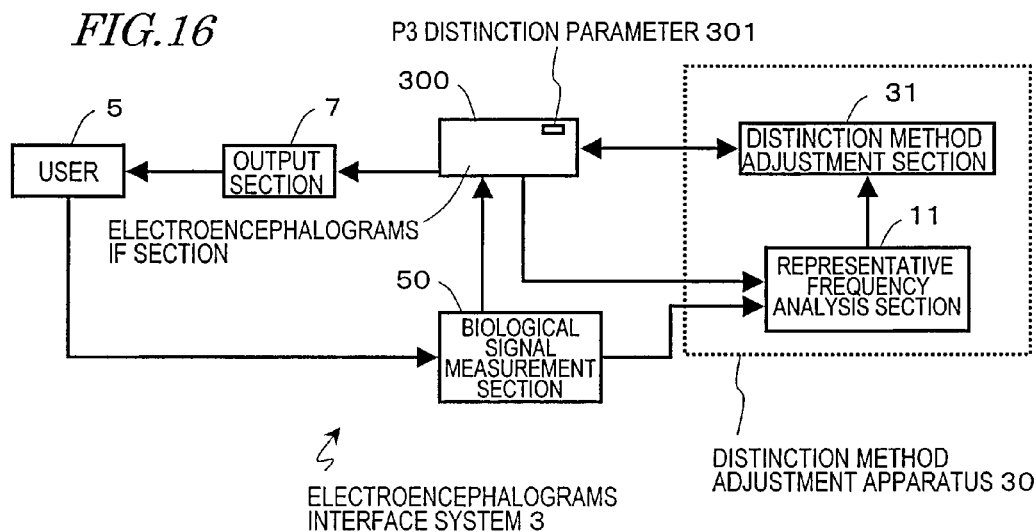
FIG. 16 A diagram showing a functional block construction of an electroencephalogram interface system 3 according to Embodiment 3.

FIG. 16 shows a functional block construction of an electroencephalogram interface system 3 of the present embodiment. FIG. 16 also shows functional blocks of the distinction method adjustment apparatus 30. The user 5 block is illustrated for the sake of explanation.

The electroencephalogram interface system 3 differs from the electroencephalogram interface system 1 (FIG. 9) of Embodiment 1 in that: instead of the electroencephalogram interface section 100 of Embodiment 1, an electroencephalogram interface section 300 whose distinction parameter for the P3 component is variable based on a P3 distinction parameter 301; and, instead of the distinction necessity determination apparatus 10 of Embodiment 1, there is provided a distinction method adjustment apparatus 30 having as a component element a distinction method adjustment section 31 which determines the distinction parameter for the P3 component based on the representative frequency. Note that, among the component elements of the electroencephalogram interface system 3, component elements which are identical to those of the electroencephalogram interface system 1 (FIG. 9) will be denoted by like reference numerals and the descriptions thereof will be omitted.

The electroencephalogram interface section 300 (hereinafter referred to as "electroencephalogram IF section 300"), which expands the functions of the electroencephalogram interface section 100, has an internal P3 distinction parameter 301, and distinguishes the P3 component after highlighting by adjusting the distinction method based on the P3 distinction parameter 301.

The P3 distinction parameter 301 is a parameter (threshold value) to be used when distinguishing the P3 component after highlighting. As described earlier (e.g. step S105 in FIG. 3), there are various distinction methods for the P3 component, but the distinction parameter may be a threshold value concerning a zone average potential or a correlation coefficient, for example, according to the distinction method.

The distinction method adjustment section 31 calculates a relative quantity (a difference or ratio) between the switching frequency ($\theta s$) received from the electroencephalogram IF section 300 and the representative frequency ($\theta e$) received from the representative frequency analysis section 11, at which the electroencephalogram frequency power of the user 5 becomes maximal, and determines whether the two are interrelated or not. The determination method is similar to that of the determination section 12 in FIG. 9. When it is determined that $\theta s$ and $\theta e$ are interrelated, the distinction method adjustment section 31 does not perform anything. On the other hand, when it is determined that the two are not interrelated, the distinction method adjustment section 31 adjusts the distinction method in the electroencephalogram interface section 300.

As used herein, to "adjust the distinction method" means changing the P3 distinction parameter 301 (threshold value) retained in the electroencephalogram IF section 300 in a direction such that the P3 component becomes less likely to be detected. For example, in the case of making a distinction by using a zone average potential in the electroencephalogram IF section 300, the threshold value is changed in the plus direction. In the case where a correlation coefficient is used to make a distinction, the threshold value is changed in the direction of becoming closer to 1.

As a method for causing the change, for example, the P3 distinction parameter 301 retained in the electroencephalogram IF section 300 may be directly rewritten externally, or the electroencephalogram IF section 300 may be instructed to change the P3 distinction parameter 301.

Note that, although the interrelation between $\theta s$ and $\theta e$ is determined herein based on the two states of "interrelated" or "not interrelated", the threshold value may be changed in a gradual or stepwise manner according to the degree of matching between $\theta s$ and $\theta e$, without being limited to two states.

Thus, adjusting the parameter for the P3 component distinction based on the representative frequency restores the possibility of detecting the user's intent of selection with the P3 component after highlighting, even in the case where an erroneous determination is made as to whether or not the highlights have been looked at. As a result, a more accurate distinction can be realized.

As will be understood from the above description, the distinction method adjustment section 31 first determines whether or not to make a distinction, similarly to the operations of the "determination section 12" (FIG. 9) and the "distinction subject menu determination section 21" (FIG. 12) described in Embodiments 1 and 2. Therefore, it can be said that, besides the functions of a determination section, e.g., the "determination section 12" (FIG. 9) and the "distinction subject menu determination section 21", the distinction method adjustment section 31 further has an additional function.

Next, with reference to the flowchart of FIG. 17, the overall processing procedure which is performed in the electroencephalogram interface system 3 will be described.

Figure 17:
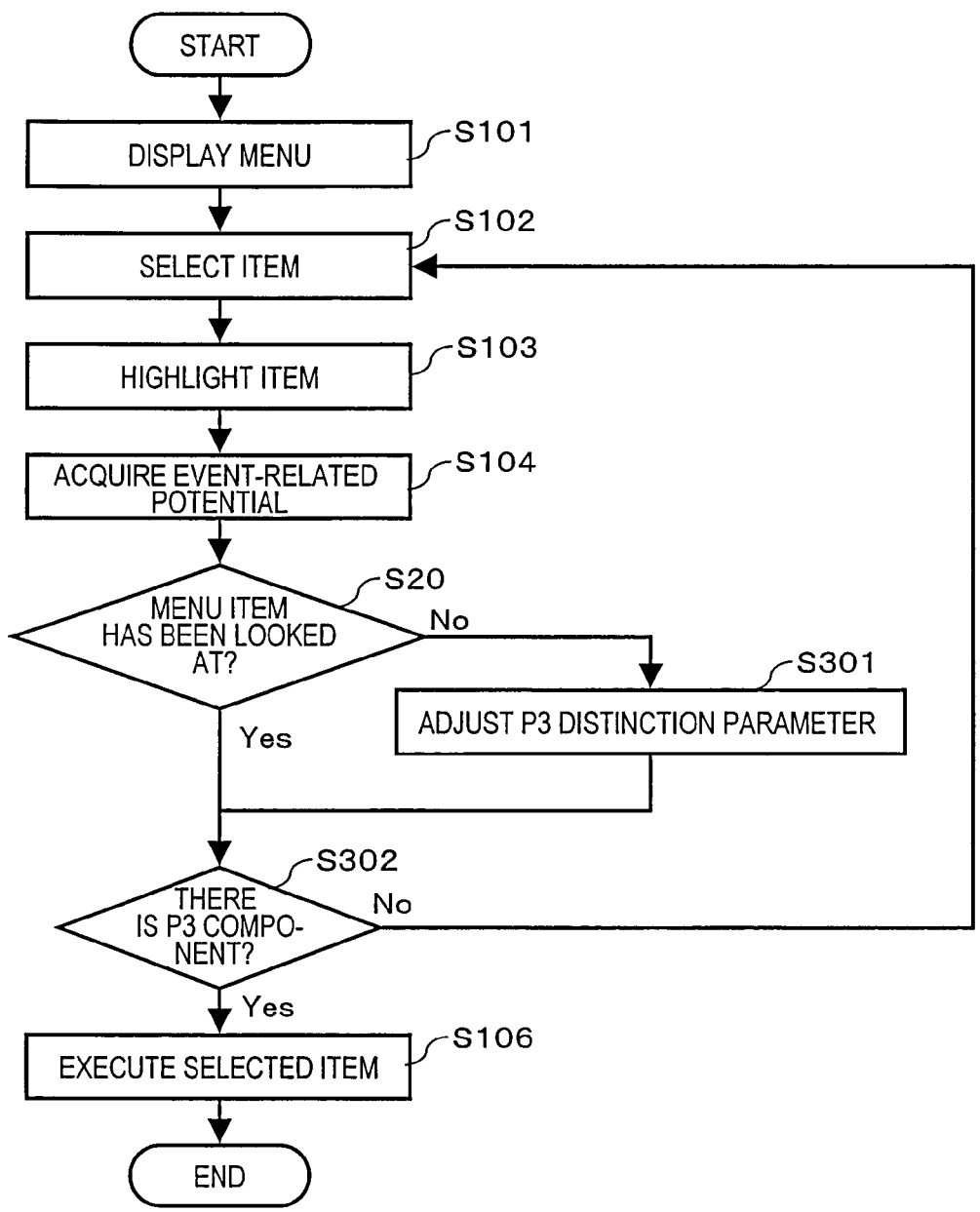
FIG. 17 A flowchart showing a processing procedure by an electroencephalogram interface system 3 according to Embodiment 3.

FIG. 17 shows a processing procedure by the electroencephalogram interface system 2 of the present embodiment. In FIG. 17, any step where the same process as in the processing by the electroencephalogram interface system 1 (FIG. 10) is performed is denoted by the same reference numeral, and the description thereof is omitted.

At step S301, the distinction method adjustment section 31 adjusts the P3 distinction parameter 301 in the electroencephalogram IF section 300 so that the P3 component becomes less likely to be detected.

At step S302, the electroencephalogram IF section 300 acquires a threshold value for P3 component detection by referring to the P3 distinction parameter 301, and based on the acquired threshold value, performs a distinction as to whether the P3 component appears in the event-related potential measured at step S104 or not.

Through such processing, even in the case where an erroneous determination is made as to whether the highlights have been looked at or not, the user's intent of selection can be detected based on the P3 component after highlighting. Note that, although the determination as to whether the user has been looking at the highlights is made in terms of two states by using the representative frequency in FIG. 17, the threshold value may be changed in a gradual or stepwise manner according to the degree of matching between θs and θe, without being limited to two states.

By providing the distinction method adjustment apparatus 30 in the electroencephalogram interface system 3 of the present embodiment, it becomes possible to adjust the parameter for P3 component distinction based on the representative frequency, thus realizing a distinction using the representative frequency and the P3 component. The representative frequency and the P3 component are both susceptible to influences of noises. However, a distinction which is immune to noise influences becomes possible by using both, whereby a reduction in the device operations that are not intended by the user can be realized.

INDUSTRIAL APPLICABILITY

With a distinction necessity determination apparatus and an electroencephalogram interface system incorporating the distinction necessity determination apparatus according to the present invention, without adding a line-of-sight detection apparatus or the like, it becomes possible to detect when a user is not looking at a menu, based on the frequency of the electroencephalogram of the user manipulating the electroencephalogram interface. As a result, by excluding the case where the user is not looking at the menu from the subject of distinction, it becomes possible to reduce device operations which are not intended by the user. Such functions of the distinction necessity determination apparatus can be realized by a computer program, for example. A computer program can exhibit the above-described functions by being read and executed by a computer, and thus will not require significant alterations of the system and will be easy to implement.

The invention claimed is:

1. An apparatus in an electroencephalogram interface system, the system having
an output section for visually presenting a manipulation menu for a device,
a biological signal measurement section for acquiring an electroencephalogram signal from a user, and
an electroencephalogram interface section for presenting via the output section menu items of the manipulation menu with a specific switching frequency, wherein the switching frequency is the frequency at which the menu items are presented, and distinguishing a component of an event-related potential which is contained in the electroencephalogram signal after each menu item is highlighted, and operating the device based on the distinguished event-related potential,
the apparatus for adjusting a distinction method for the electroencephalogram signal to be adopted in the electroencephalogram interface section comprising:
a frequency analysis section for calculating a representative frequency at which a frequency power of the electroencephalogram signal becomes maximal; and
a determination section for calculating a relative quantity between the switching frequency of the menu items and the representative frequency of the electroencephalogram signal, and comparing the relative quantity to a threshold value to determine whether the representative frequency is related to switching of the menu items or not, and in accordance with the result of the determination, outputting to the electroencephalogram interface section an instruction to adjust the distinction method for the electroencephalogram signal to be adopted in the electroencephalogram interface section.

2. The apparatus of claim 1, wherein,
the determination section
instructs the electroencephalogram interface section to adopt the electroencephalogram signal as subject of distinction when the representative frequency is determined as being related to switching of the menu items,
and instructs the electroencephalogram interface section to exclude the electroencephalogram signal from the subject of distinction when the representative frequency is determined as not being related to switching of the menu items.

3. The apparatus of claim 1, wherein, based on a difference between the switching frequency of menu items and the representative frequency of the electroencephalogram signal, or a ratio between the switching frequency of menu items and the representative frequency of the electroencephalogram signal, the determination section determines whether the representative frequency is related to switching of the menu items or not.

4. The apparatus of claim 1, wherein the frequency analysis section calculates the representative frequency based on an electroencephalogram signal acquired at or after a point in time which is a predetermined number of seconds before a point of highlighting each menu item.

5. The apparatus of claim 1, wherein, as the representative frequency, the frequency analysis section calculates a frequency at which the frequency power becomes largest in a predetermined frequency band containing the switching frequency of menu items.

6. The apparatus of claim 1, wherein, as the representative frequency, the frequency analysis section calculates a frequency at which the frequency power becomes largest in a frequency band of 0.5 Hz or above.

7. The apparatus of claim 6, wherein the determination section determines whether the representative frequency is related to switching of the menu items or not based on a relative quantity of the switching frequency being selected from a frequency band of 0.5 Hz to 9 Hz and the representative frequency of the electroencephalogram signal.

8. The apparatus of claim 7, wherein the determination section determines that the representative frequency is not related to switching of the menu items when a difference between the switching frequency of menu items and the representative frequency of the electroencephalogram signal is 0.2 Hz or more.

9. The apparatus of claim 1, wherein, when the determination section instructs the electroencephalogram interface section to exclude the electroencephalogram signal from the subject of distinction, the electroencephalogram interface section sets back an operating state of the device by one.

10. The apparatus of claim 1, wherein,
when the electroencephalogram interface section presents menu items of a plurality of kinds of manipulation menus at a plurality of respectively different switching frequencies,
the determination section determines whether or not the representative frequency is related to the switching of any one of the menu items of the manipulation menus based on a relative quantity between each of the plurality of switching frequencies and the representative frequency of the electroencephalogram signal.

11. The apparatus of claim 10, wherein the determination section determines whether or not the representative frequency is related to the switching of any one of the menu items of the manipulation menus based on a relative quantity between each of the plurality of switching frequencies being set so as not to be integer multiples of one another and the representative frequency of the electroencephalogram signal.

12. The apparatus of claim 10, wherein the determination section identifies a switching frequency corresponding to a smallest relative quantity among relative quantities between the plurality of switching frequencies and the representative frequency of the electroencephalogram signal, and determines whether or not the representative frequency is related to switching of the menu items presented at the identified switching frequency.

13. The apparatus of claim 12, wherein,
the determination section retains a threshold value corresponding to each of the plurality of switching frequencies; and
the determination section determines that the representative frequency is related to switching of the menu items presented at the identified switching frequency when the smallest relative quantity is smaller than the threshold value corresponding to the identified switching frequency, and determines that the representative frequency is not related to switching of the menu items presented at the identified switching frequency when the smallest relative quantity is equal to or greater than the threshold value corresponding to the identified switching frequency.

14. The apparatus of claim 1, wherein,
the electroencephalogram interface section retains a threshold value for distinguishing whether a P3 component is contained in the event-related potential contained in the electroencephalogram signal after each menu item is highlighted; and
when it is determined that the representative frequency is not related to switching of the menu items, the determination section changes the size of the threshold value in a direction such that the P3 component of the event-related potential becomes less likely to be detected.

15. In an electroencephalogram interface system having
an output section for visually presenting a manipulation menu for a device,
a biological signal measurement section for acquiring an electroencephalogram signal from a user, and
an electroencephalogram interface section for presenting via the output section menu items of the manipulation menu with a specific switching frequency, wherein the switching frequency is the frequency at which the menu items are presented, and distinguishing a component of an event-related potential which is contained in the electroencephalogram signal after each menu item is highlighted, and operating the device based on the distinguished event-related potential,
a distinction necessity determination method for determining whether or not to allow the electroencephalogram interface section to perform a distinction of the electroencephalogram signal, comprising the steps of:
calculating as a representative frequency at which a frequency power of the electroencephalogram signal becomes maximal; and
calculating a relative quantity between the switching frequency of the menu items and the representative frequency of the electroencephalogram signal, and comparing the relative quantity to a threshold value to determine whether the representative frequency is related to switching of the menu items or not;
instructing, when it is determined as being related, the electroencephalogram interface section to adopt the electroencephalogram signal as subject of distinction; and
instructing, when it is determined as not being related, the electroencephalogram interface section to exclude the electroencephalogram signal from the subject of distinction.

16. The distinction necessity determination method of claim 15, wherein,
when the electroencephalogram interface section presents menu items of a plurality of kinds of manipulation menus at a plurality of respectively different switching frequencies,
the determining step determines whether or not the representative frequency is related to the switching of the menu items of the manipulation menus based on a relative quantity between each of the plurality of switching frequencies and the representative frequency of the electroencephalogram signal.

17. The distinction necessity determination method of claim 16, wherein the determining step identifies a switching frequency corresponding to a smallest relative quantity among relative quantities between the plurality of switching frequencies and the representative frequency of the electroencephalogram signal, and determines whether the representative frequency is related to switching of the menu items presented at the identified switching frequency.

18. The distinction necessity determination method of claim 17, further comprising a step of providing a threshold value for each of the plurality of switching frequencies, wherein,
the determining step determines that the representative frequency is related to switching of the menu items presented at the identified switching frequency when the smallest relative quantity is smaller than the threshold value corresponding to the identified switching frequency, and determines that the representative frequency is not related to switching of the menu items presented at the identified switching frequency when the smallest relative quantity is equal to or greater than the threshold value corresponding to the identified switching frequency.

19. An apparatus in an electroencephalogram interface system, the system having
- an output section for visually presenting a manipulation menu for a device,
- a biological signal measurement section for acquiring an electroencephalogram signal from a user, and
- an electroencephalogram interface section for presenting via the output section menu items of the manipulation menu with a specific switching frequency, wherein the switching frequency is the frequency at which the menu items are presented, and distinguishing a component of an event-related potential which is contained in the electroencephalogram signal after each menu item is highlighted, and operating the device based on the distinguished event-related potential, the apparatus for adjusting a distinction method for the electroencephalogram signal to be adopted in the electroencephalogram interface section, comprising:
- a frequency analysis section for calculating a representative frequency at which a frequency power of the electroencephalogram signal becomes maximal; and
- a determination section for calculating a relative quantity between the switching frequency of menu items and the representative frequency of the electroencephalogram signal, and comparing the relative quantity to a threshold value to determine whether the representative frequency is related to switching of the menu items or not, judging that the user is looking at the menu item when the representative frequency is determined as being related and judging that the user is not looking at the menu item when the representative frequency is determined as not being related, and adjusting the distinction method of the electroencephalogram interface section for the electroencephalogram signal in accordance with the result of determination.

* * * * *